(12) United States Patent
Hu et al.

(10) Patent No.: US 6,562,485 B2
(45) Date of Patent: May 13, 2003

(54) ELECTROLUMINESCENT (EL) DEVICES

(75) Inventors: Nan-Xing Hu, Oakville (CA); Hany Aziz, Burlington (CA); Poonam Jain, Barrie (CA); Zoran D. Popovic, Mississauga (CA)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 10/232,558

(22) Filed: Aug. 29, 2002

(65) Prior Publication Data

US 2003/0044646 A1 Mar. 6, 2003

Related U.S. Application Data

(62) Division of application No. 09/771,311, filed on Jan. 26, 2001, now Pat. No. 6,479,172.

(51) Int. Cl.$^7$ ............................................. H05B 33/14
(52) U.S. Cl. ..................... 428/690; 428/704; 428/917; 257/40; 257/103; 313/504; 313/506; 252/301.16; 252/301.35
(58) Field of Search ..................... 428/690, 704, 428/917; 257/40, 103; 313/504, 506; 252/301.16, 301.35

(56) References Cited

U.S. PATENT DOCUMENTS

| | | | |
|---|---|---|---|
| 3,172,862 A | 3/1965 | Gurnee et al. | 252/301.3 |
| 3,530,325 A | 9/1970 | Mehl et al. | 313/108 |
| 4,356,429 A | 10/1982 | Tang | 313/503 |
| 4,539,507 A | 9/1985 | VanSlyke et al. | 313/504 |
| 4,720,432 A | 1/1988 | VanSlyke et al. | 428/457 |
| 4,769,292 A | 9/1988 | Tang et al. | 428/690 |
| 4,885,211 A | 12/1989 | Tang et al. | 428/457 |
| 5,150,006 A | 9/1992 | Van Slyke et al. | 313/504 |
| 5,151,629 A | 9/1992 | VanSlyke | 313/504 |
| 5,409,783 A | 4/1995 | Tang et al. | 428/690 |
| 5,429,884 A | 7/1995 | Namiki et al. | 428/690 |
| 5,516,577 A | 5/1996 | Matsuura et al. | 428/212 |
| 5,635,308 A * | 6/1997 | Inoue et al. | 428/690 |
| 5,846,666 A | 12/1998 | Hu et al. | 428/690 |
| 5,891,587 A | 4/1999 | Hu et al. | 428/690 |
| 5,925,472 A | 7/1999 | Hu et al. | 428/690 |
| 5,932,363 A | 8/1999 | Hu et al. | 428/690 |
| 5,935,721 A * | 8/1999 | Shi et al. | 428/690 |
| 5,942,340 A | 8/1999 | Hu et al. | 428/690 |
| 5,952,115 A | 9/1999 | Hu et al. | 428/690 |
| 6,057,048 A | 5/2000 | Hu et al. | 428/690 |
| 6,169,163 B1 * | 1/2001 | Woo et al. | 528/397 |

FOREIGN PATENT DOCUMENTS

JP 7-157473 * 6/1995 ......... C07D/251/24

* cited by examiner

Primary Examiner—Deborah Jones
Assistant Examiner—Ling Xu
(74) Attorney, Agent, or Firm—Robert Thompson

(57) ABSTRACT

An electroluminescent device containing an anode, an organic electroluminescent element, and a cathode wherein the electroluminescent element contains, for example, a fluorescent hydrocarbon component of Formula (I)

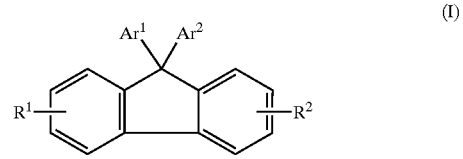

Figure 1:
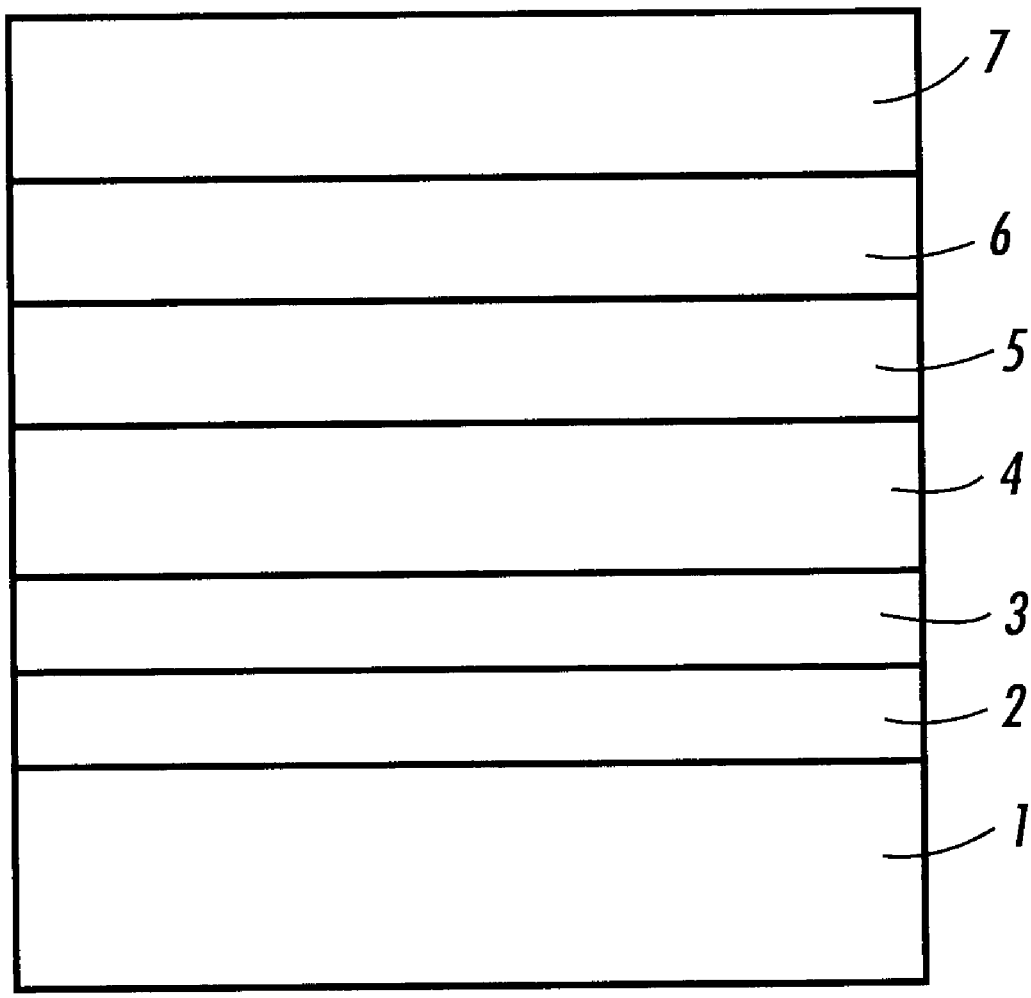

wherein $R^1$ and $R^2$ are substituents, which are selected from the group consisting of hydrogen, an alkyl, an alicyclic alkyl, an alkoxy, a halogen, and a cyano; $Ar^1$ and $Ar^2$ are each independently an aromatic component or an aryl group comprised of a from about 4 to about 15 conjugate-bonded or fused benzene rings.

21 Claims, 1 Drawing Sheet

ELECTROLUMINESCENT (EL) DEVICES

CROSS-REFERENCE TO RELATED APPLICATIONS

This is a Divisional of application Ser. No. 09/771,311; filed on Jan. 26, 2001, now U.S. Pat. No. 6,479,172.

RELATED COPENDING APPLICATIONS AND PATENTS

Illustrated in copending applications U.S. Ser. No. 09/770,159, filed Jan. 26, 2001, the disclosure of which is totally incorporated herein by reference, is an organic light emitting device comprising in an optional sequence (i) a substrate;

(ii) a first electrode;

(iii) a mixed region comprising a mixture of a hole transport material and an electron transport material, and wherein this mixed region includes at least one organic luminescent material;

(iv) a second electrode;

(v) a thermal protective element coated on the second electrode; wherein, one of the two said first and second electrodes is a hole injection anode, and one of the two said electrodes is an electron injection cathode, and wherein the organic light emitting device further comprises;

(vi) a hole transport region, interposed between the anode and the mixed region, wherein the hole transport region optionally includes a buffer layer; and (vii) an electron transport region interposed between the second electrode and the mixed region; and in U.S. Ser. No. 09/770,154, filed Jan. 26, 2001, the disclosure of which is totally incorporated herein by reference, is an organic light emitting device comprising in sequence a substrate;

a first electrode;

a light-emitting region comprising an organic luminescent material; and a second electrode.

Illustrated in U.S. Pat. Nos. 5,942,340; 5,952,115; 5,932,363; 5,925,472, and 5,891,587, the disclosures of which are totally incorporated herein by reference, are EL devices. In U.S. Pat. No. 5,925,472, the disclosures of which are totally incorporated herein by reference, there are disclosed organic EL devices with blue luminescent materials comprised of metal chelates of oxadiazole compounds, and which devices may provide a greenish blue color.

Illustrated in U.S. Pat. No. 6,057,048, the disclosure of which is totally incorporated herein by reference, is an electroluminescent device comprised of an anode, a hole transporting layer, a light emitting layer, and a cathode, wherein said light emitting layer contains a component of the formula

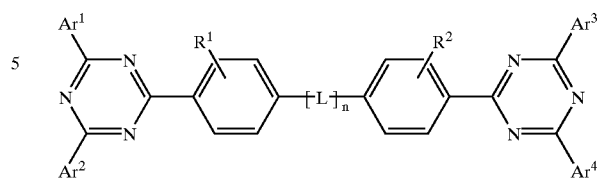

(I)

wherein $Ar^1$, $Ar^2$, $Ar^3$, and $Ar^4$ are each independently aryl or optionally aliphatic; $R^1$ and $R^2$ are independently selected from the group consisting of hydrogen, aliphatic, halogen, and cyano; L is a suitable linking group; and n is a number of from 0 to about 3.

The appropriate components and processes of the above patents and copending applications may be selected for the present invention in embodiments thereof.

BACKGROUND OF THE INVENTION

This invention is directed to organic electroluminescent (EL) devices, and more specifically, to organic EL devices with a number of excellent performance characteristics inclusive of the enablement of blue emitting EL devices, which devices contain luminescent components or a luminescent component with excellent high thermal stability, film forming characteristics and intense blue fluorescence. Organic EL devices are desired that are capable of providing uniform luminescence, saturated color especially in the blue regions of the visible spectrum, and low driving voltages. The organic EL devices of the present invention enable in embodiments the above characteristics and which devices contain organic luminescent materials or light emitting components comprised of fluorescent hydrocarbon compounds, and which devices can be selected for use in flat-panel emissive display technologies, including TV screens, computer screens, and the like.

PRIOR ART

A simple organic EL device can be comprised of a layer of an organic luminescent material conductively sandwiched between an anode, typically comprised of a transparent conductor, such as indium tin oxide, and a cathode, typically a low work function metal such as magnesium, calcium, aluminum, or the alloys thereof with other metals. The EL device functions on the principle that under an electric field, positive charges (holes) and negative charges (electrons) are respectively injected from the anode and cathode into the luminescent layer and undergo recombination to form excitonic states which subsequently emit light. A number of prior art organic EL devices have been prepared from a laminate of an organic luminescent material and electrodes of opposite polarity, which devices include a single crystal material, such as single crystal anthracene, as the luminescent substance as described, for example, in U.S. Pat. No. 3,530,325. However, these devices usually require excitation voltages on the order of 100 volts or greater.

In U.S. Pat. No. 4,539,507 there is disclosed an EL device formed of a conductive glass transparent anode, a hole transporting layer of 1,1-bis(4-p-tolylaminophenyl) cyclohexane, an electron transporting layer of 4,4'-bis(5,7-di-tert-pentyl-2-benzoxzolyl)stilben, and an indium cathode.

U.S. Pat. No. 4,720,432 discloses an organic EL device comprising a dual-layer hole injecting and transporting zone, one layer being comprised of porphyrinic compounds supporting hole injection and the other layer being comprised of aromatic tertiary amine compounds supporting hole transport.

U.S. Pat. No. 4,769,292 discloses an EL device employing a luminescent zone comprised of an organic host material capable of sustaining hole-electron recombination and a fluorescent dye material capable of emitting light in response to energy released by hole-electron recombination. A preferred host material is an aluminum complex of 8-hydroxyquinoline, namely tris(8-hydroxyquinolinate) aluminum.

While recent progress in organic EL research has elevated the potential of organic EL devices for widespread applications, the performance levels of a number of current available devices, especially with respect to blue emission, may still be below expectations. Further, for visual display applications, organic luminescent materials should provide a satisfactory color in the visible spectrum, normally with emission maxima at about 460, 550 and 630 nanometers for blue, green and red. These organic EL devices may comprise a light-emitting layer which is comprised of a host material doped with a guest fluorescent material that is responsible for color emission. For efficient down-shifting of EL emission wavelength in the host-guest emitting layer, it may be desirable that the host material should fluorescence in the blue or shorter wavelength region. In many conventional organic EL devices, the luminescent zone or layer is formed of a green-emitting luminophor of tris(8-hydroxyquinolinate)aluminum with certain fluorescent materials. U.S. Pat. No. 5,409,783 discloses a red-emitting organic EL device by doping the tris(8-hydroxyquinolinate) aluminum layer with a red fluorescent dye. However, up-shifting of the tris(8-hydroxyquinolinate)aluminum emission to blue region is believed to be highly inefficient. Although there have been. several disclosures describing blue-emitting organic EL devices, for example in U.S. Pat. Nos. 5,151,629 and 5,516,577, the disclosures of which are totally incorporated herein by reference, their performance characteristics still possess many disadvantages such as poor emission hue, high operation voltages, low luminance, and poor operation stability. Thus, there continues to be a need for improved luminescent compositions for organic EL devices, which may vacuum evaporable and form thin films with excellent thermal stability. There is also a need for luminescent compositions which are capable of providing uniform and satisfactory emission in the blue region of the light spectrum. In particular, there is a need for efficient blue luminescent materials for organic EL devices, which may optionally be doped with a fluorescent dye. Further, there is also a need for luminescent compositions which can enhance charge transporting characteristics, thus lowering device driving voltages. Therefore, a primary feature of the present invention is to provide luminescent materials comprised of certain fluorescent hydrocarbon compounds, which in comparison to certain EL devices comprised of the metal chelates of oxadiazole compounds can provide improved and excellent emission characteristics particularly in the blue region, such as a saturated blue color and a narrow emission spectrum.

SUMMARY OF THE INVENTION

It is a feature of the present invention to provide luminescent compositions for organic EL devices.

It is another feature of the present invention to provide organic EL devices with many advantages, such as low operation voltages, uniform light emission with spectrum spreading from blue to longer wavelengths, thermal stability, electrochemical stability, and charge transport capability.

In an another feature of the present invention there are provided organic EL devices with a light emitting layer containing a luminescent material comprised of novel fluorescent hydrocarbon compounds.

In yet another feature of the present invention there are provided organic EL devices with a light-emitting layer comprised of a luminescent hydrocarbon compound.

Further, in a feature of the present invention there are provided organic EL devices comprised of a supporting substrate of, for example, glass, an anode, an optional buffer layer, a vacuum deposited organic hole transporting layer comprised of, for example, 4,4'-bis-(9-carbazolyl)-1,1-biphenyl, a vacuum deposited light emitting layer comprised of a luminescent hydrocarbon compound, an optional vacuum deposited electron transporting layer, and in contact therewith a low work function metal, such as magnesium, lithium, and their alloys as a cathode.

Yet in another feature of the present invention there is provided an organic EL device comprised of a supporting substrate of, for example, glass, an anode, an optional buffer layer, a vacuum deposited organic hole transporting layer comprised of tertiary aromatic amines, for example, N,N'-1-naphthyl-N,N'-diphenyl-1,1'-biphenyl-4,4'-diamine, a vacuum deposited light emitting layer, an optional vacuum deposited electron transporting layer, and in contact therewith a low work function metal, such as magnesium and its alloys as a cathode, wherein the light emitting layer is comprised of a mixture of a novel hydrocarbon compound as a host component and an optional fluorescent material.

These and the other features of the present invention are accomplished by the provision of luminescent or light emitting components comprised of the hydrocarbon compounds illustrated by the Formula (I)

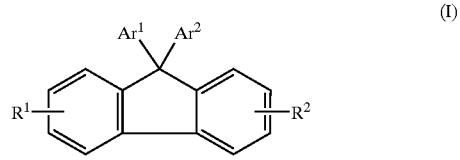

wherein $R^1$ and $R^2$ are substituents, which may be selected from the group consisting of hydrogen, an alkyl group with, for example, from 1 to about 25, and more specifically, to about 6 carbon atoms, an aryl group with about 6 to about 30 carbon atoms, an alkoxy group with from 1 to about 25, and more specifically, to about 6 carbon atoms, a halogen, a cyano group and the like; $Ar^1$ and $Ar^2$ are each an aromatic component, such as an aryl group with, for example, about 4 to about 10 conjugate-bonded or fused benzene rings, and which may be independently selected, for example, from the group consisting of those as represented by or encompassed by the following formulas

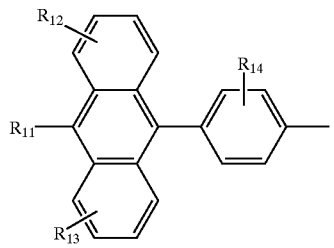

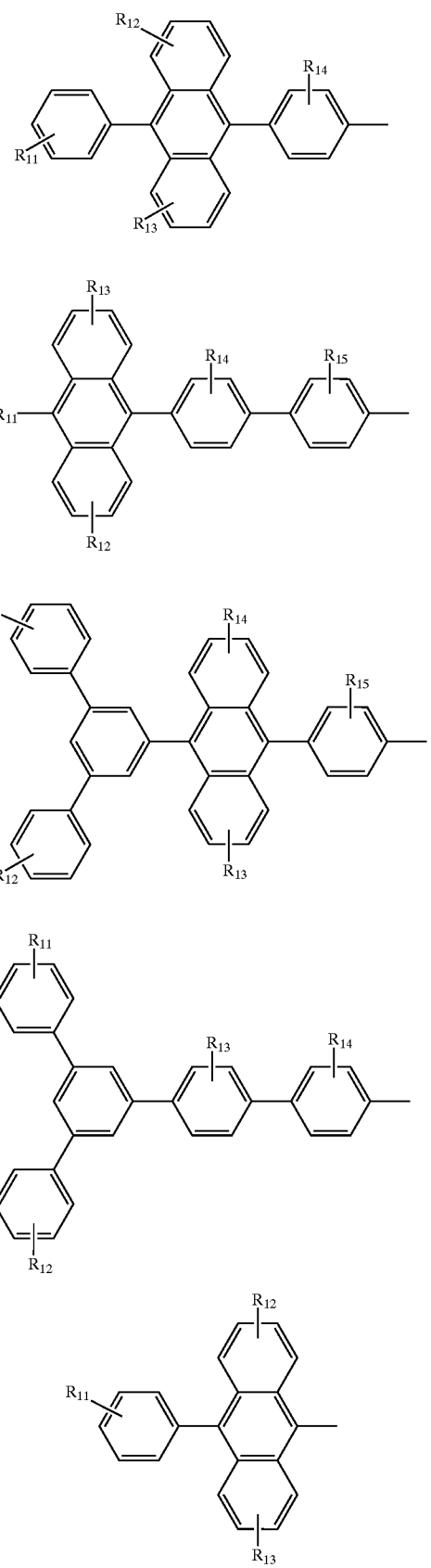

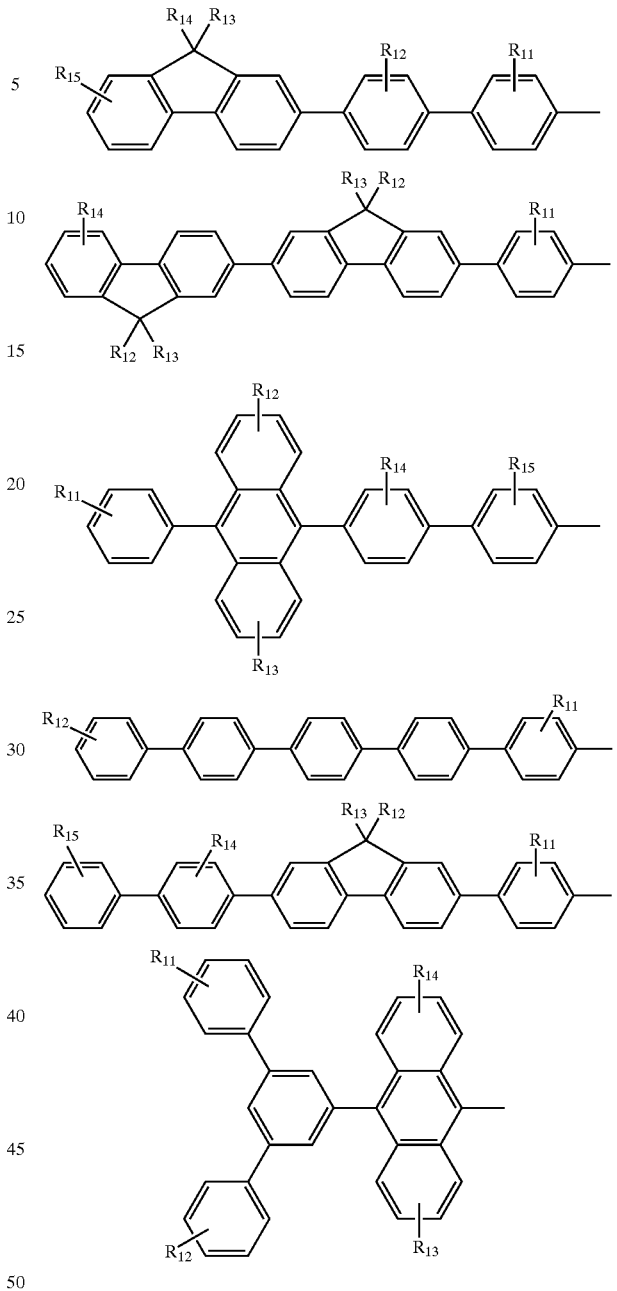

wherein $R_{11}$, $R_{12}$, $R_{13}$, $R_{14}$, and $R_{15}$ are each a substituent selected from the group consisting of hydrogen, an alkyl group with, for example, from 1 to about 6 carbon atoms, an alicyclic alkyl group with from about 3 to about 15 carbon atoms, an alkoxy group with, for example, preferably from 1 to about 6 carbon atoms, a dialkylamino group with preferably from about 1 to about 3 carbon atoms, a halogen, a cyano group and the like.

The features of the present invention can be also accomplished by the provision of luminescent or light emitting components comprised of the hydrocarbon compounds illustrated by Formula (II)

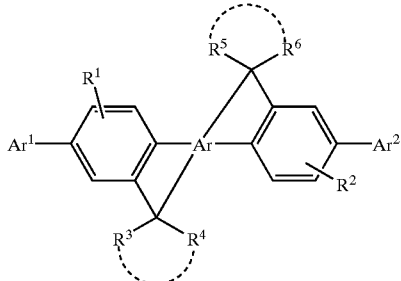

(II)

wherein $R^1$ and $R^2$ are substituents, which may be selected from the group consisting of hydrogen, an alkyl group with, for example, preferably from 1 to about 6 carbon atoms, an alicyclic alkyl group with from about 3 to about 15 carbon atoms, an aryl group with about 6 to about 30 carbon atoms, an alkoxy group with preferably from 1 to about 6 carbon atoms, a halogen, a cyano group and the like; $R^3$, $R^4$, $R^5$, and $R^6$ are each a substituent, which may be selected from the group consisting of hydrogen, an alkyl group with, for example, preferably from 1 to about 6 carbon atoms, an alicyclic alkyl group with from about 3 to about 15 carbon atoms, an aryl group with about 6 to about 30 carbon atoms, an alkoxy group with preferably from 1 to about 6 carbon atoms, and the like, wherein $R^3$ and $R^4$, or $R^4$ and $R^5$ may optionally be combined into a bivalent hydrocarbon group, and is, for example, selected from the group consisting of an alkylene group with from about 3 to about 8 carbon atoms, an alkylidene group with from about 3 to about 15 carbon atoms, an alicyclic alkylidene group with from about 3 to about 15 carbon atoms, and a arylalkylidene group with from about 6 to about 30 carbon atoms, and the like; $Ar^1$ and $Ar^2$ are each an aromatic component, such as an aryl group with from about 6 to about 30 carbon atoms, or an arylvinyl group with from about 6 to about 30 carbon atoms, which may, for example, be selected from the group consisting of a phenyl, a biphenylyl, a 3,5-diarylphenyl, a phenylvinyl, a diphenylvinyl, and the like; and wherein Ar is a tetravalent aromatic group with, for example, from about 6 to about 60 carbon atoms, and which group may selected, for example, from the group consisting of the following formulas

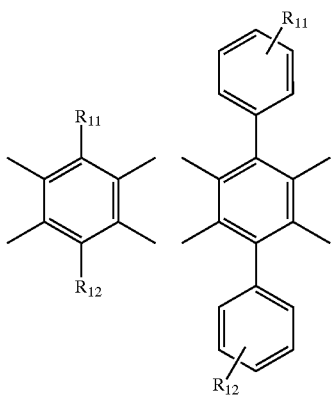

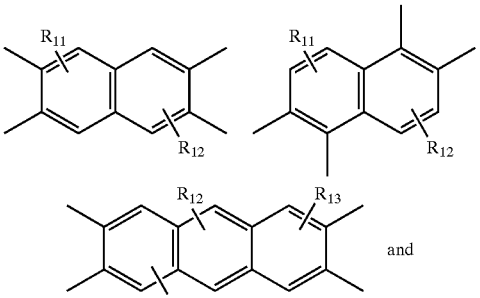

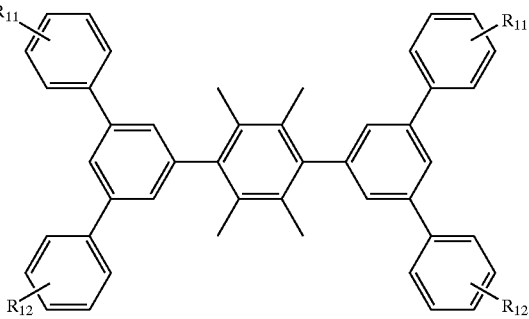

and wherein $R_{11}$, $R_{12}$, and $R_{13}$ are each a substituent, which may be selected from the group consisting of hydrogen, an alkyl group with, for example, preferably from 1 to about 6 carbon atoms, an alicyclic alkyl group with from about 3 to about 15 carbon atoms, an alkoxy group with, for example, preferably from 1 to about 6 carbon atoms, a dialkylamino group with preferably from about 1 to about 3 carbon atoms, a halogen, a cyano group and the like.

In embodiments, the present invention relates to organic EL devices that are comprised in the following order of a supporting substrate of, for example, glass, an anode, an optional buffer layer, an organic hole transporting layer, an organic light emitting hydrocarbon layer, and an optional electron transporting layer, and in contact therewith a low work function metal as a cathode, wherein the light emitting layer contains at least one luminescent hydrocarbon compound illustrated and encompassed by the formulas recited herein, for example (I) and (II); and layered EL devices with a light emitting layer comprised of a luminescent composition comprised of a hydrocarbon compound illustrated by, for example, Formulas (I) and (II) as a host component capable of sustaining hole-electron recombination and a guest fluorescent material capable of emitting light in response to energy released by the hole-electron recombination. The light emitting layer may be formed by vacuum deposition from evaporation of the fluorescent hydrocarbon material, and wherein the presence of the fluorescent material permits a wide latitude of wavelengths of light emission and may enable the enhancement of electroluminescent efficiency and improvements in device operation stability.

The luminescent or light emitting hydrocarbon materials illustrated herein possess in embodiments several advantages. For example, the hydrocarbon compounds exhibit strong fluorescence in the solid state in the region of from about 400 nanometers to longer wavelengths of, for example, about 600 nanometers; they have the ability of forming thin films with excellent thermal stability by vacuum evaporation; they are stable; and they can also be blended with a number of fluorescent materials to form a common phase.

FIGURES

The FIGURE illustrates an EL device or an organic light emitting diode which is comprised of a supporting substrate 1 of, for example, glass; an anode 2 of, for example, indium tin oxide in a thickness of from about 1 to about 100 nanometers and preferably from about 10 to about 80 nanometers (throughout the thickness ranges for each layer are examples and other suitable thickness may be selected); optionally a buffer layer 3 of, for example, copper (II) phthalocyanine in a thickness of from about 5 to about 80 nanometers and preferably from about 10 to about 40 nanometers; an organic hole transporting layer 4 of an aromatic amine compound, for example N,N'-1-naphthyl-N, N'-diphenyl-1,1'-biphenyl-4,4'-diamine in a thickness of from about 1 to about 100 nanometers and preferably from about 5 to about 80 nanometers; an organic light emitting layer 5 comprised of a luminescent hydrocarbon compound of the formulas or encompassed by the formulas illustrated herein in a thickness of from about 1 to about 100 nanometers and preferably from about 20 to about 80 nanometers; an organic electron transporting layer or hole blocking layer 6 of, for example, 4,4'-bis-[2-(4,6-diphenyl-1,3,5-triazinyl)]-1,1'-biphenyl or tris-(8-hydroxyquinolinato) aluminum in a thickness of from about 1 to about 300 nanometers and preferably from about 10 to about 80 nanometers, and in contact therewith a low work function metal as a cathode 7. In this EL device, a junction is formed between the hole transporting layer and the light emitting layer. In operation, when the anode is electrically biased to a positive potential with respect to the cathode, holes are injected into the organic hole transporting layer and transported across this layer to the junction. Concurrently, electrons are injected from the cathode to the electron transport layer and are transported toward the same junction. Recombination of holes and electron occurs near the junction resulting in light emission. Optionally, the light emitting layer can contain more than one luminescent hydrocarbon compound illustrated and encompassed by the Formulas recited herein, for example (I) and (II); and layered EL devices with a light emitting layer comprised of a luminescent composition comprised of a hydrocarbon compound illustrated by, for example, Formulas (I) and (II) as a host component capable of sustaining hole-electron recombination and a guest fluorescent material capable of emitting light in response to energy released by the hole-electron recombination.

DESCRIPTION OF EMBODIMENTS

In aspects thereof, the present invention relates to an organic electroluminescent device comprised of an anode and a cathode, and an EL element positioned between the anode and the cathode, wherein the EL element has at least a light emitting layer containing a luminescent hydrocarbon compound of the Formula (I)

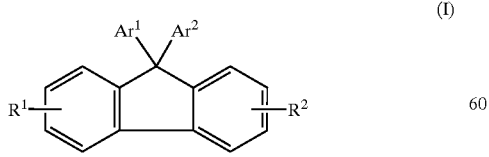

(I)

wherein $R^1$ and $R^2$ are substituents, which may be selected from the group consisting of hydrogen, an alkyl group with, for example, from 1 to about 6 carbon atoms, an aryl group with about 6 to about 30 carbon atoms, an alkoxy group with preferably from 1 to about 6 carbon atoms, a halogen, a cyano group and the like. Specific examples of substituents for $R^1$ and $R^2$ are hydrogen, methyl, tert-butyl, a phenyl, a biphenylyl, and the like; $Ar^1$ and $Ar^2$ in Formula (I) are each an aromatic component, such as an aryl group with, for example, about 4 to about 10 conjugate-bonded or fused benzene rings, and which may be independently selected, for example, from the group consisting of those of the following formulas

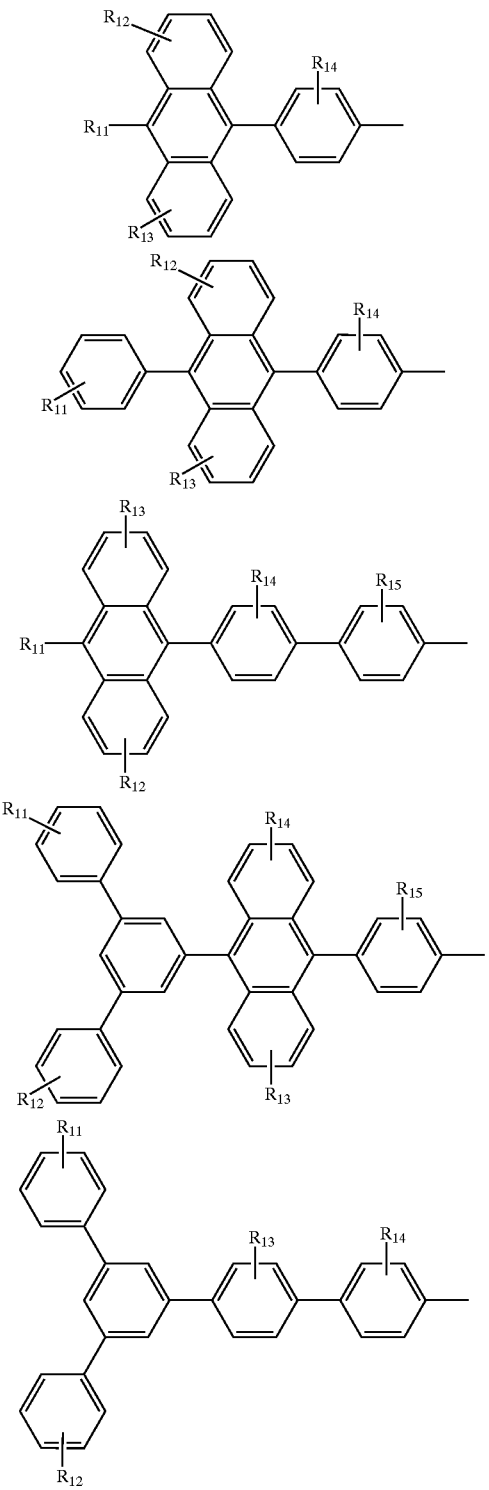

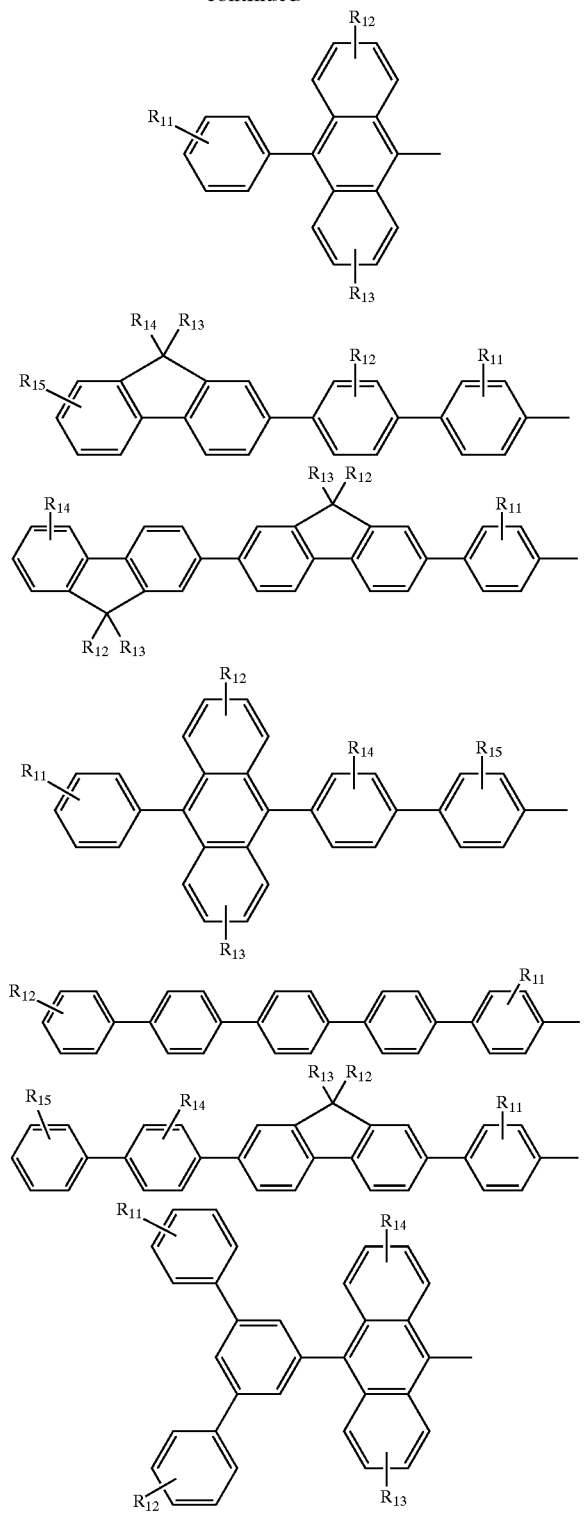

wherein $R_{11}$, $R_{12}$, $R_{13}$, $R_{14}$, and $R_{15}$ are each a substituent selected from the group consisting of hydrogen, an alkyl group with, for example, preferably from 1 to about 6 carbon atoms, an alicyclic alkyl group with from about 3 to about 15 carbon atoms, an alkoxy group with, for example, preferably from 1 to about 6 carbon atoms, a dialkylamino group with preferably from about 1 to about 3 carbon atoms, a halogen, a cyano group and the like. Illustrative examples of alkyl group are methyl, ethyl, tert-butyl and the like; illustrative examples of alicyclic alkyl group are cyclopentyl, cyclohexyl, 4-tert-butylcyclohexyl, and the like; typical examples of alkoxy group include methoxy, ethoxy, isopropoxy, tert-butoxy, and the like. Useful examples of substituents for $R_{11}$, $R_{12}$, $R_{13}$, $R_{14}$, and $R_{15}$ include hydrogen, methyl, tert-butyl, cyclohexyl, methoxy, tert-butoxy, fluorine, cyano and the like.

Also, in embodiments the present invention is directed to an electroluminescent device comprised of a first electrode like an anode, an organic electroluminescent element, and a second electrode like a cathode wherein said electroluminescent element contains a fluorescent hydrocarbon component of Formula (I)

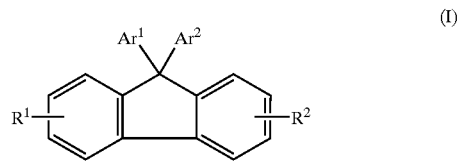

(I)

wherein $R^1$ and $R^2$ are substituents selected from the group consisting of hydrogen, an alkyl, an alicyclic alkyl, an alkoxy, a halogen, and a cyano; $Ar^1$ and $Ar^2$ are each independently an aromatic component or an aryl group comprised, for example, of from about 4 to about 15 conjugate-bonded or fused benzene rings; an electroluminescent device wherein $Ar^1$ and $Ar^2$ are independently selected from the group consisting of

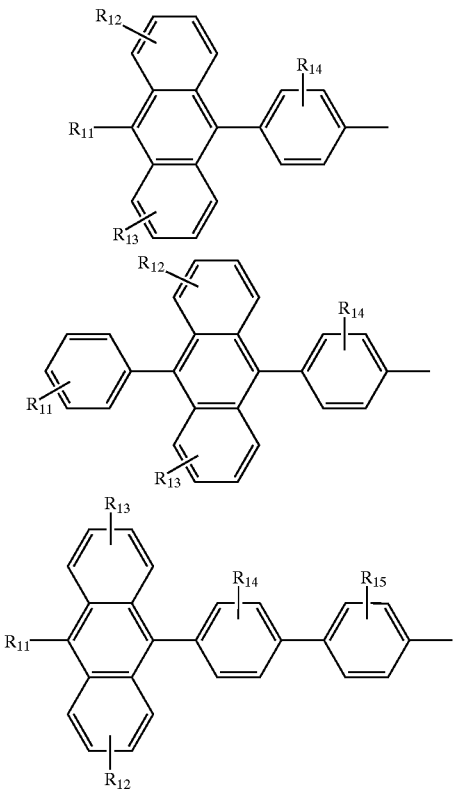

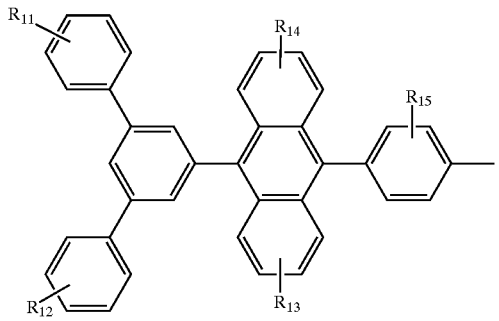

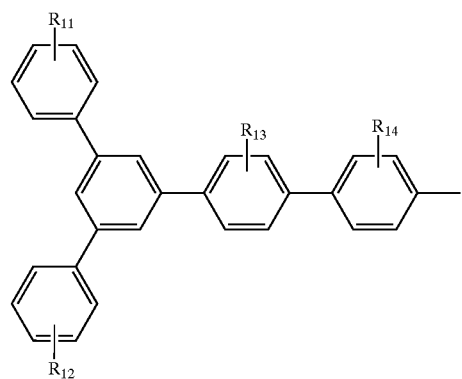

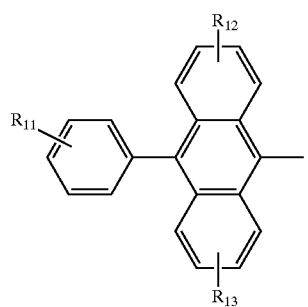

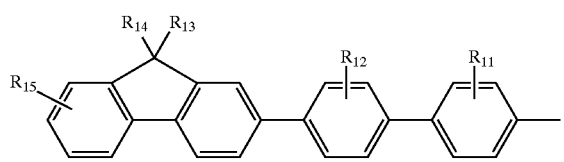

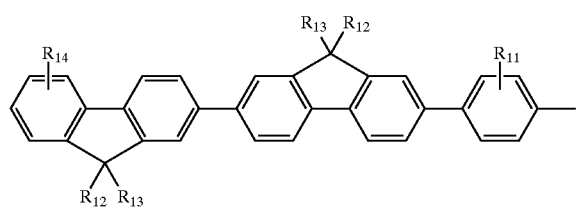

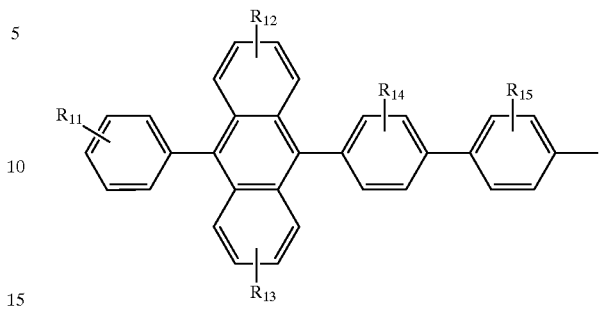

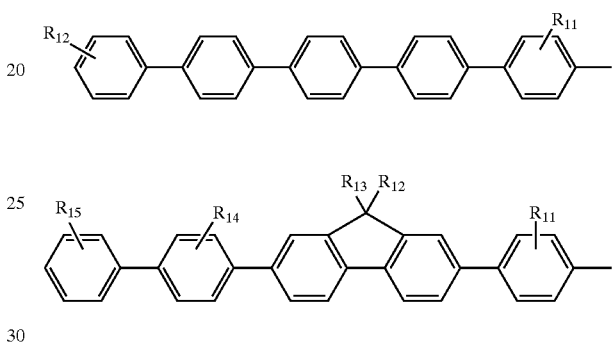

and

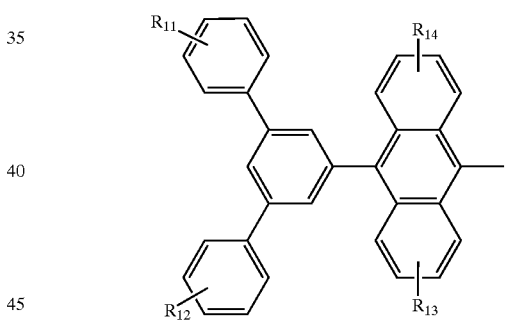

wherein $R_{11}$, $R_{12}$, $R_{13}$, $R_{14}$, and $R_{15}$ are each a substituent selected from the group consisting of hydrogen, alkyl with, for example, from 1 to about 6 carbon atoms, an alicyclic alkyl group with, for example, from about 3 to about 15 carbon atoms, an alkoxy group with from 1 to about 6 carbon atoms, a dialkylamino group with from about 2 to about 6 carbon atoms, a halogen, and a cyano group; an electroluminescent device wherein the $R^1$ and $R^2$ are individually selected from the group consisting of methyl, ethyl, isopropyl, tert-butyl, cyclohexyl, 4-tert-butylcyclohexyl, methoxy, ethoxy, isopropoxy, tert-butoxy, dimethylamino, diethylamino, phenyl, tolyl, naphthyl, anthryl, phenylanthryl, diphenylanthryl, biphenylyl, phenylvinyl, diphenylvinyl, hydrogen, fluorine, chlorine, and cyano; an electroluminescent device wherein the $R_{11}$, $R_{12}$, $R_{13}$, $R_{14}$, and $R_{15}$ are individually selected from the group consisting of hydrogen, methyl, ethyl, isopropyl, tert-butyl, cyclohexyl, 4-tert-butylcyclohexyl, methoxy, ethoxy, isopropoxy, tert-butoxy, dimethylamino, diethylamino, fluorine, chlorine, and cyano; an electroluminescent device wherein the hydrocarbon component is selected from the group consisting of Compound (I-1)
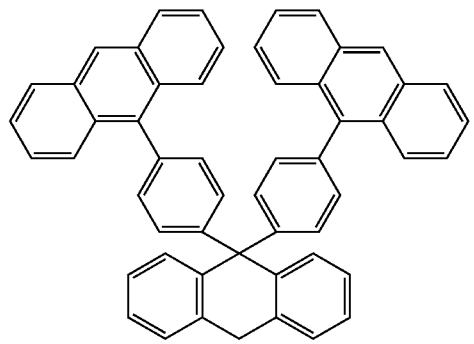
Compound (I-2)
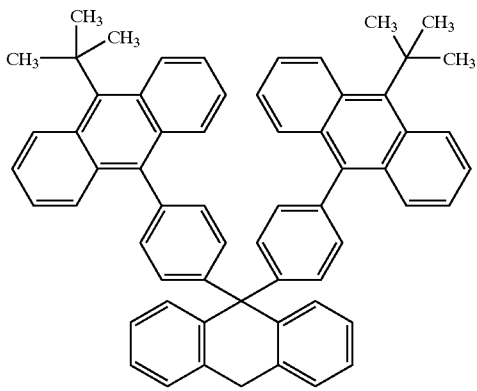
Compound (I-3)
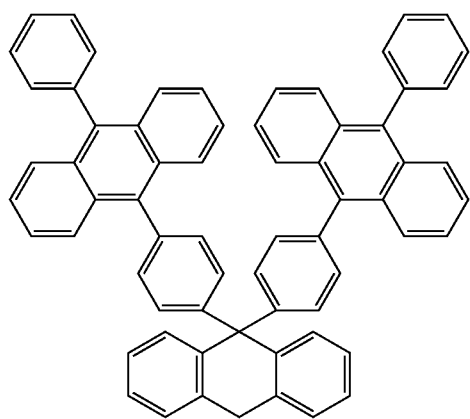
Compound (I-4)
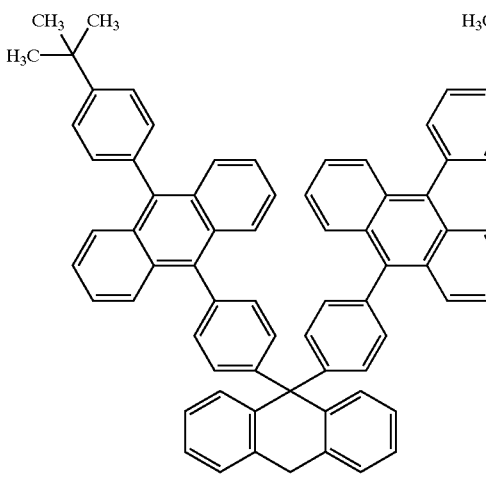
Compound (I-5)
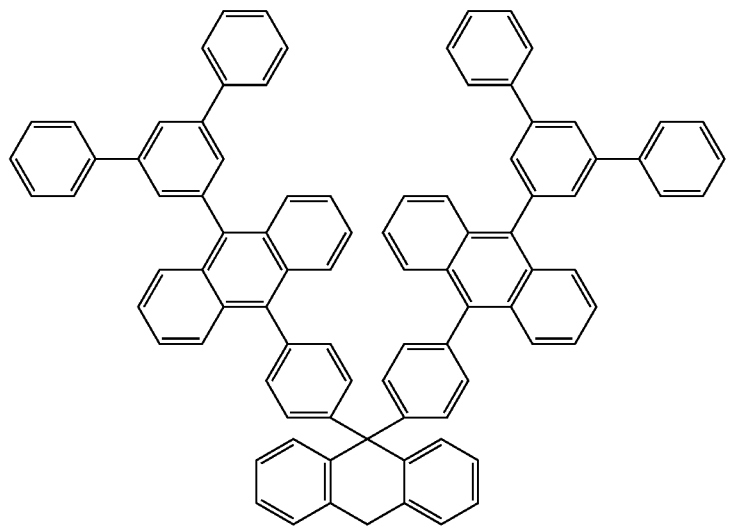

Compound (I-6)
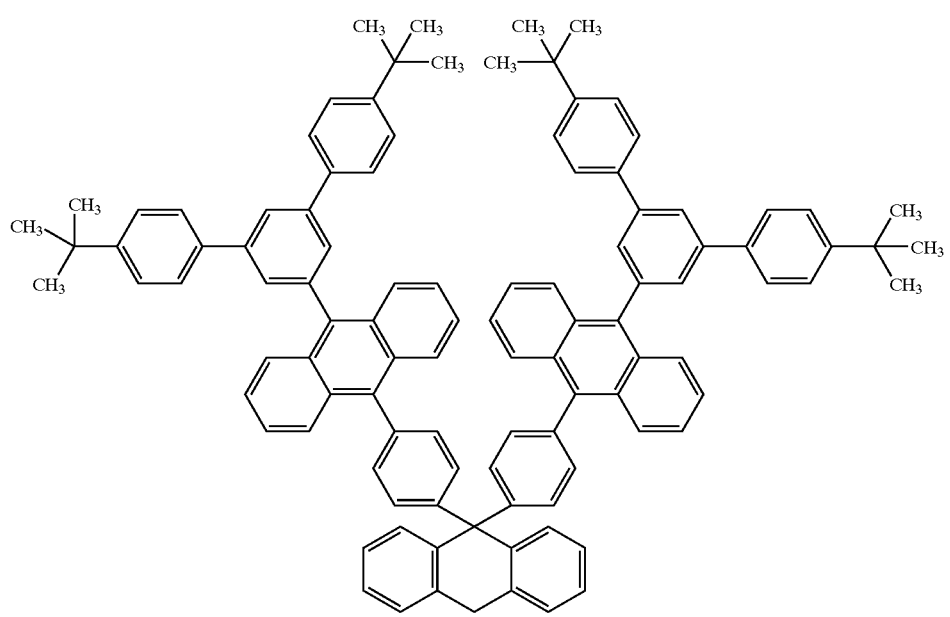
Compound (I-7)
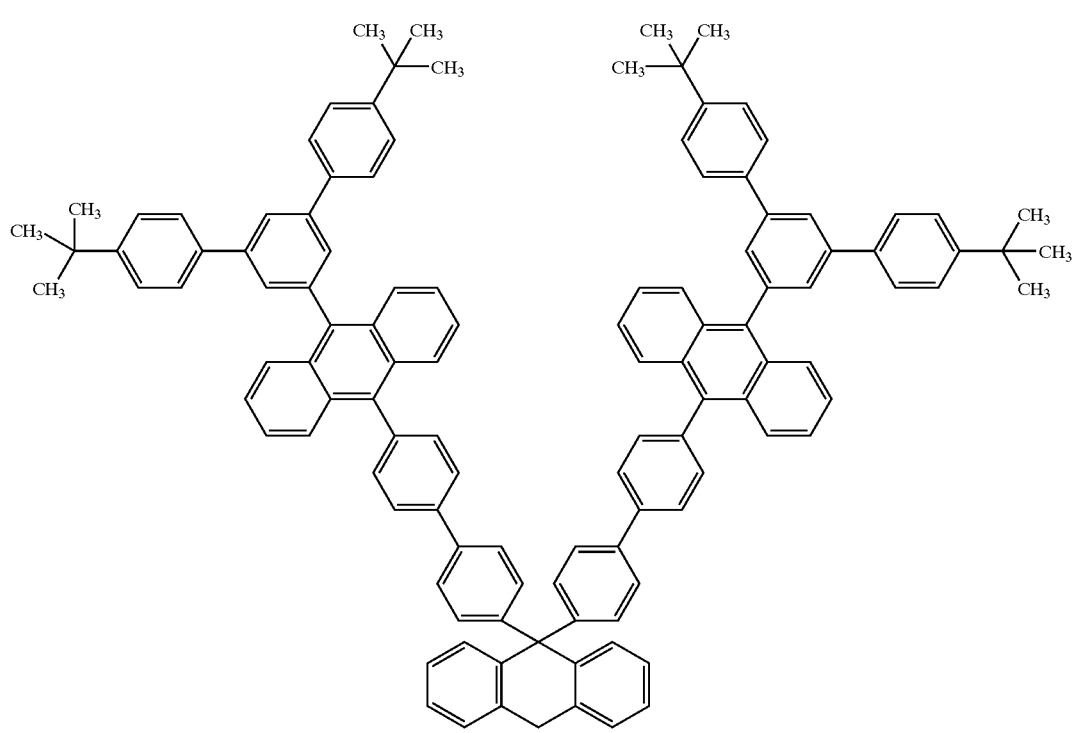

-continued

Compound (I-8)

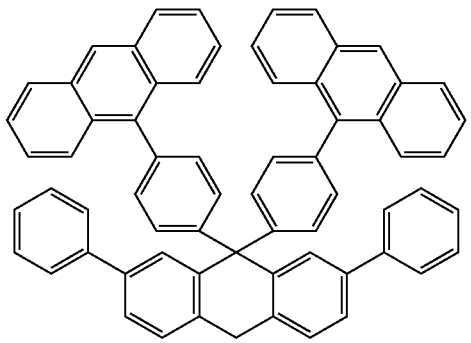

Compound (I-9)

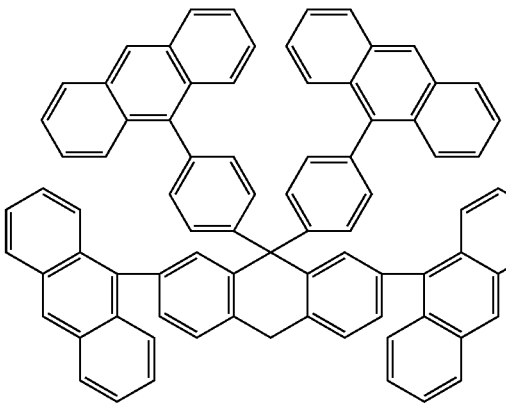

Compound (I-10)

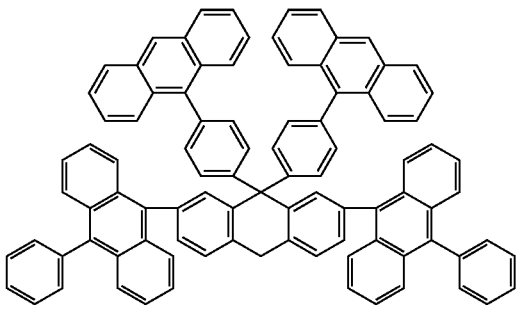

and

Compound (I-11)

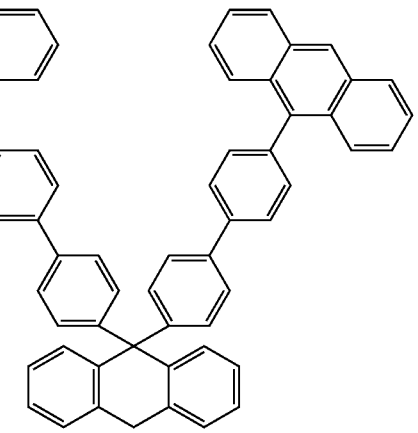

an electroluminescent device comprised of an anode, an organic electroluminescent element and a cathode, wherein the electroluminescent element is situated between the anode and the cathode, and contains a fluorescent hydrocarbon component of Formula (II)

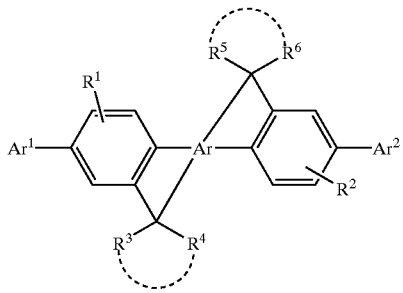

wherein $R^1$ and $R^2$ are independently selected from the group consisting of hydrogen, an alkyl group, an alicyclic alkyl group, an aryl group, an alkoxy group, a halogen, and a cyano group; $R^3$, $R^4$, $R^5$, and $R^6$ are independently selected from the group consisting of hydrogen, an alkyl group, an alicyclic alkyl group, an aryl group, and an alkoxy group, wherein $R^3$ and $R^4$, or $R^4$ and $R^5$ are optionally combined into a bivalent hydrocarbon group selected from the group consisting of an alkylene, an alkylidene, an alicyclic alkylidene, and an arylalkylidene, wherein $Ar^1$ and $Ar^2$ are independently an aryl group; and wherein Ar is an tetravalent aromatic group; an electroluminescent device wherein the $R^1$ and $R^2$ are individually selected from the group consisting of methyl, ethyl, cyclohexyl, tert-butyl, methoxy, ethoxy, tert-butoxy, phenyl, tolyl, hydrogene, fluorine, chlorine, and cyano; an electroluminescent device wherein the $R^3$, $R^4$, $R^5$ and $R^6$ are selected from the group consisting of hydrogen, methyl, ethyl, propyl, hexyl, cyclohexyl, tert-butyl, methoxy, ethoxy, 2-methoxyethyl, phenyl, tolyl, methoxyphenyl, cyclohexylidene, 4-tert-butylcyclohexylidene, benzylidene, diphenylmethylidene, and mixtures thereof; an electroluminescent device wherein $Ar^1$ and $Ar^2$ are selected from the group consisting of an aryl of phenyl, tolyl, tert-butylphenyl, methoxyphenyl, 3,5-diphenylphenyl, 3,5-bis(p-tert-butylphenyl)phenyl, biphenylyl, and 4'-methoxybiphenyl-4-yl, 2-phenylvinyl, 2,2-diphenylvinyl, and trans-stilbenyl; an electroluminescent device wherein $R_1$ to $R_6$ are each a substituent selected from the group consisting of hydrogen, an alkyl group with from 1 to about 6 carbon atoms, an alicyclic alkyl group with from about 3 to about 15 carbon atoms, an alkoxy group with from 1 to about 6 carbon atoms, a dialkylamino group with from about 1 to about 3 carbon atoms, a halogen, and cyano; an electroluminescent device wherein the substituents for $R_1$ to $R_6$ are individually selected from the group consisting of hydrogen, methyl, ethyl, isopropyl, tert-butyl, cyclohexyl, 4-tert-butylcyclohexyl, methoxy, ethoxy, isopropoxy, tert-butoxy, dimethylamino, diethylamino, fluorine, chlorine, and cyano; an electroluminescent device wherein the hydrocarbon component is selected from the group consisting of Compound (II-1)
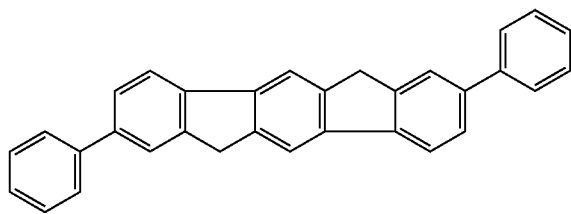
Compound (II-2)
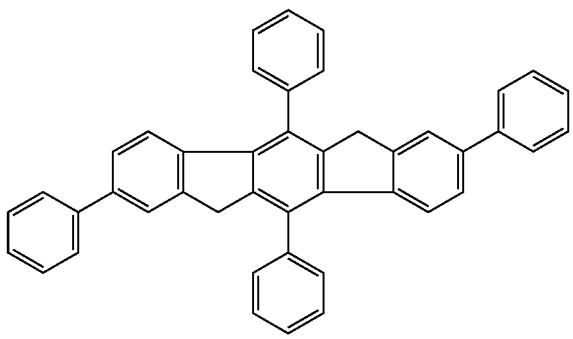
Compound (II-3)
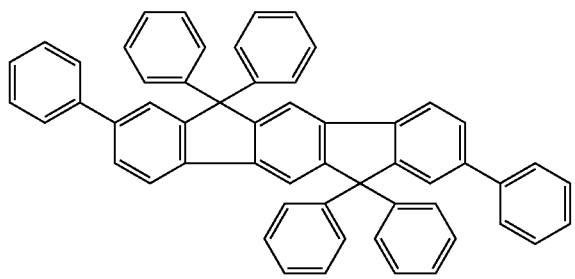
Compound (II-4)
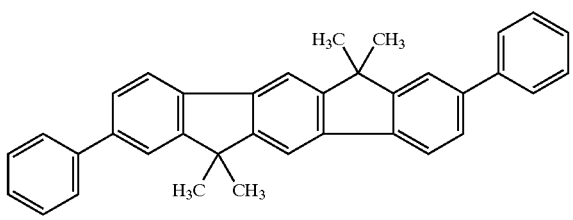
Compound (II-5)
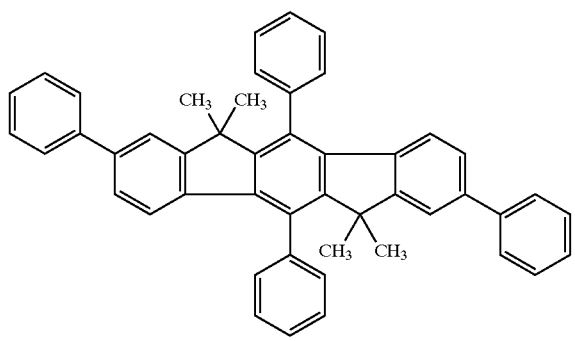
Compound (II-6)
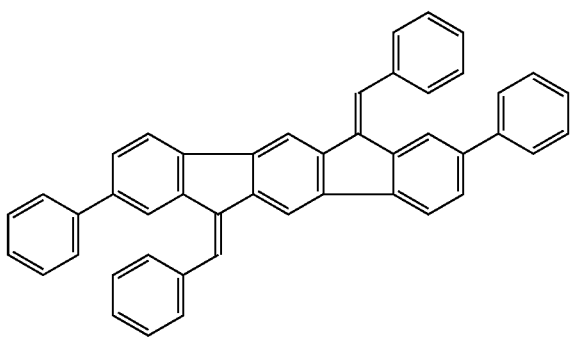
Compound (II-7)
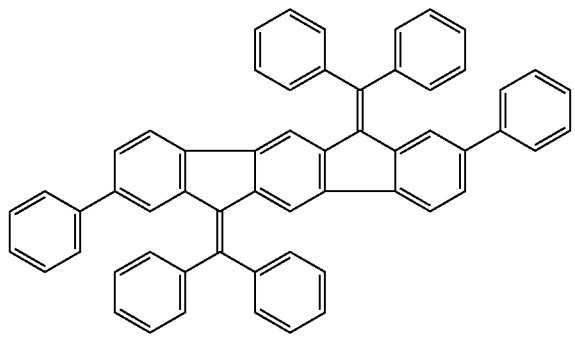
Compound (II-8)
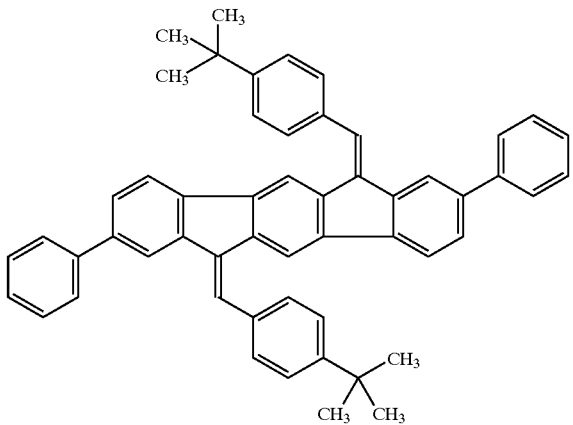

-continued
Compound (II-9)
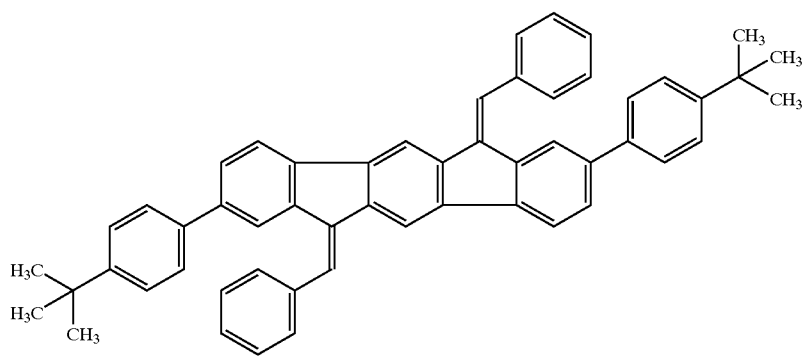
Compound (II-10)
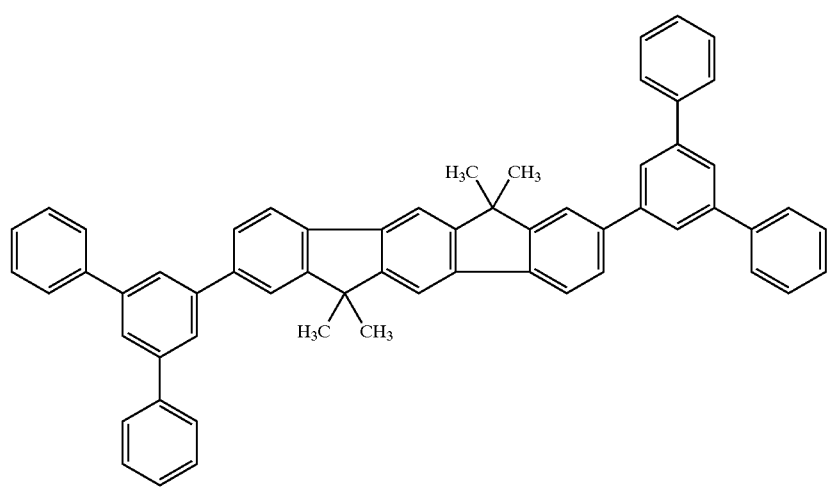
Compound (II-11)
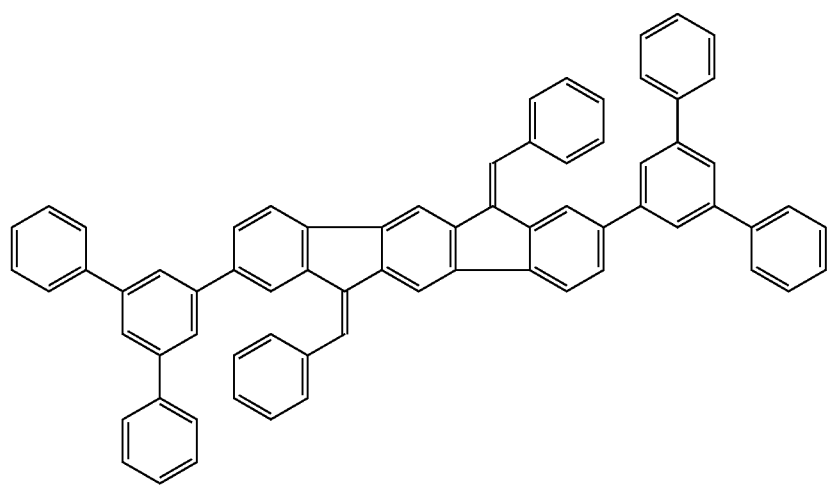

-continued
Compound (II-12)
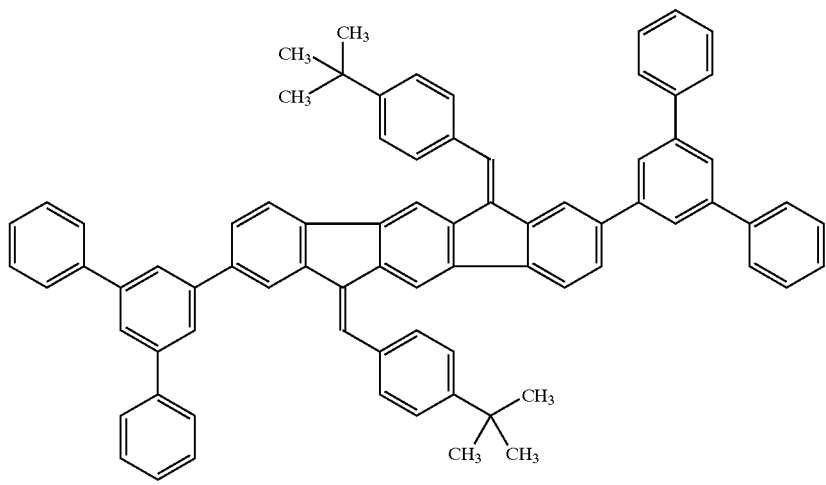
Compound (II-13)
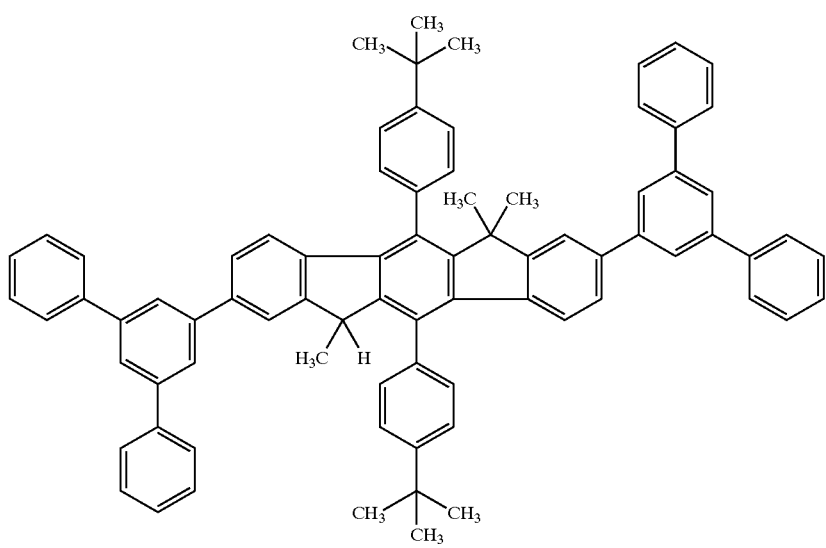
Compound (II-14)
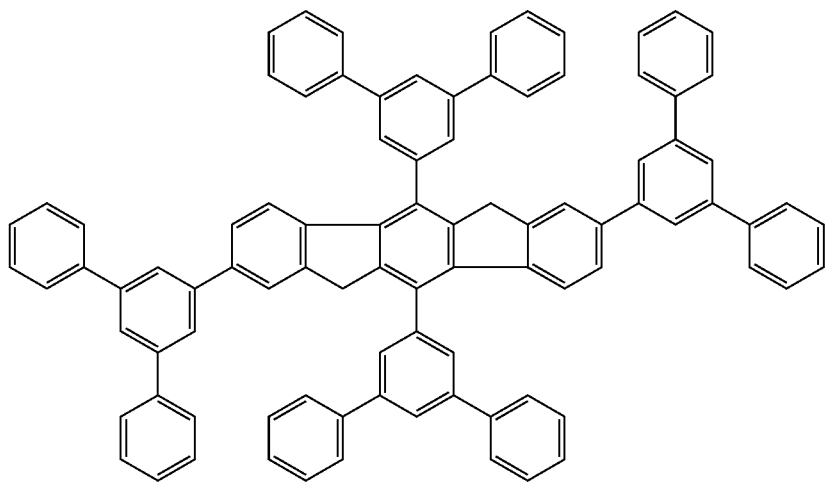

Compound (II-15)
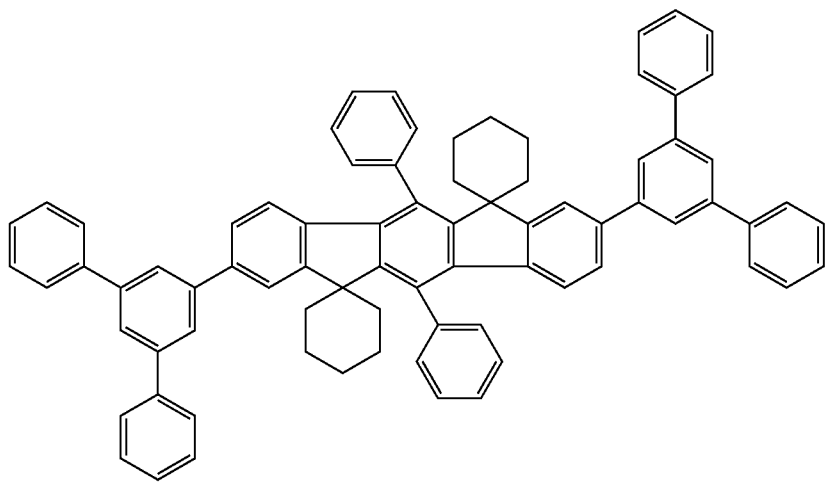
Compound (II-16)
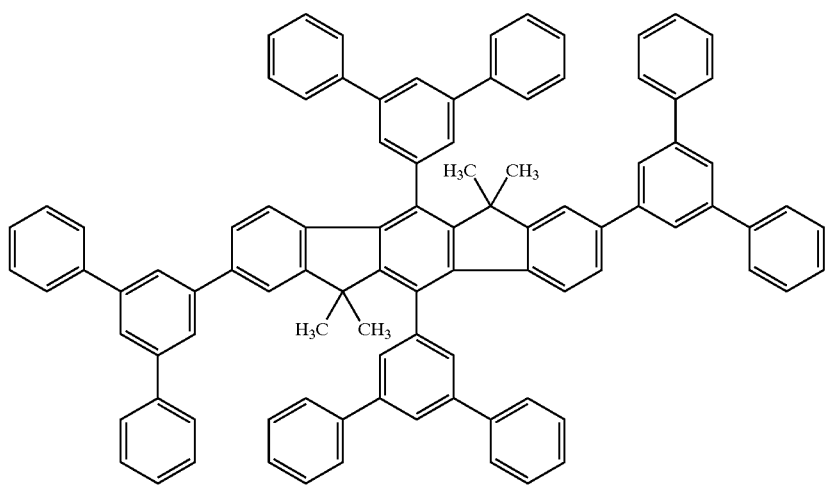
Compound (II-17)                                   Compound (II-18)
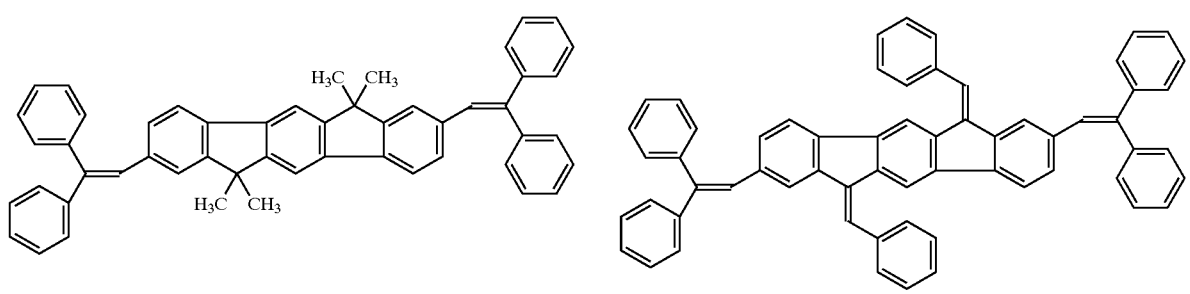
Compound (II-19)                                   Compound (II-20)
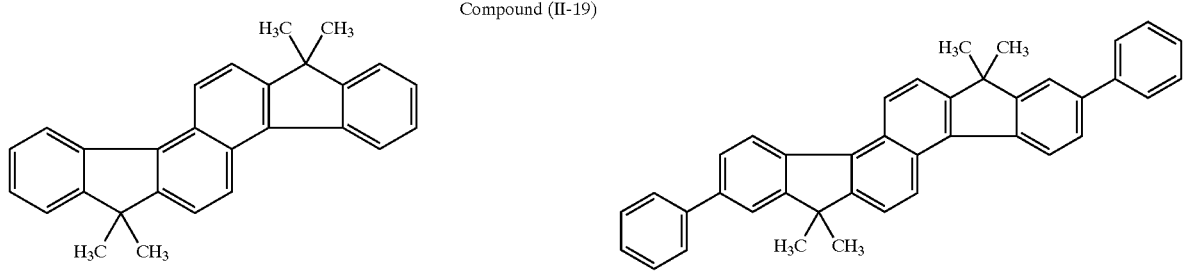

-continued

Compound (II-21)

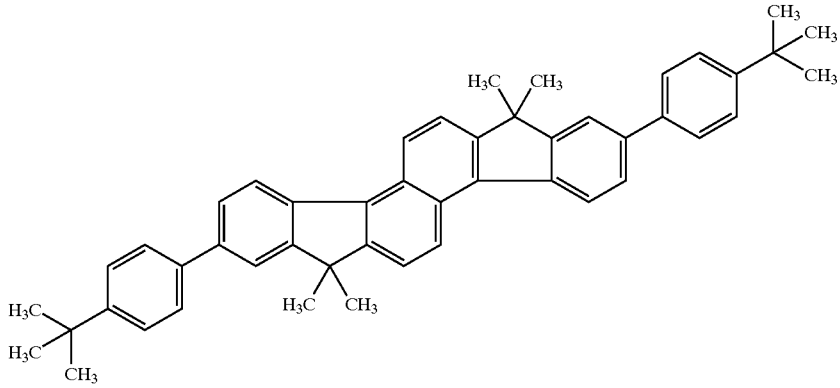

Compound (II-22)

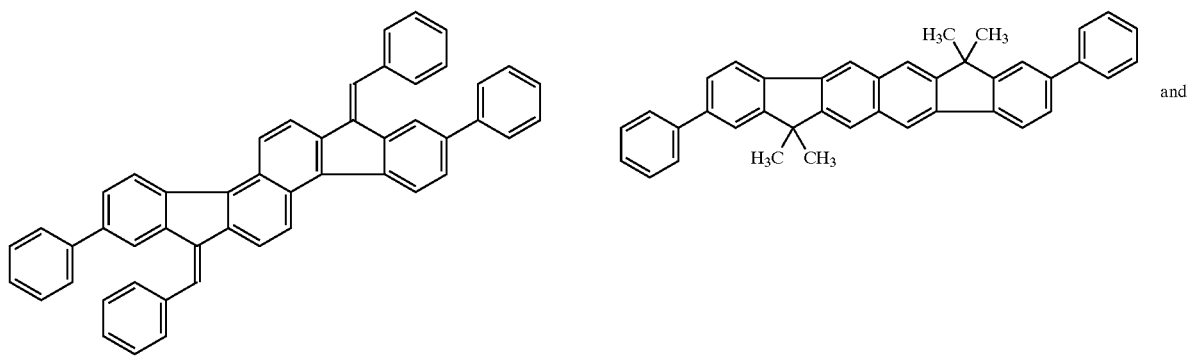

Compound (II-23)

and

Compound (II-24)

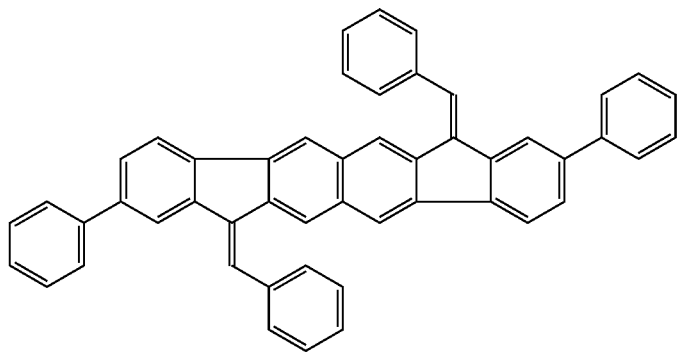

an electroluminescent device wherein the electroluminescent element includes an emitting layer comprised of a host hydrocarbon compound comprised of Formula (I), (II), or mixtures thereof, and a fluorescent dye; an electroluminescent device wherein the fluorescent dye possesses a bandgap no greater than that of the host material; an electroluminescent device wherein the fluorescent dye is selected from the group consisting of coumarins, dicyanomethylene pyranes, polymethines, oxabenzanthranes, xanthenes, pyryliums, carbostyls, perylenes, acridones, quinacridone, and fused ring aromatic fluorescent dyes; an electroluminescent device wherein the fluorescent dye is selected from the group consisting of N-methyl-9-acridone, N-methyl-2-methoxy-9-acridone, N-methyl-2-phenoxy-9-acridone, N-methyl-2-t-butoxy-9-acridone, N-phenyl-2-methoxy-9-acridone, N-methyl-2-phenyl-9-acridone, N-methyl-2-diethylamino-9-acridone, perylene, terta-tert-butylperylene, rubrene, N,N'-dimethylquinacridone, N,N'-dimethyl-2-methylquinacridone, N,N'-dimethyl-2,9-dimethylquinacridone, N,N'-dimethyl-2-chloroquinacridone, N,N'-dimethyl-2-fluoroquinacridone, and N,N'-dimethyl-1,2-benzoquinacridone; an electroluminescent device wherein the fluorescent dye is present in an amount of from about $10^{-3}$ to about 10 mole percent based on the moles of the hydrocarbon host material; an organic electroluminescent device comprising in the following sequence an anode, an optional buffer layer, a hole transporting layer, a light emitting layer comprised of a hydrocarbon compound of Formulas (I), (II) or mixtures thereof, an electron transport layer, and a cathode; an electroluminescent device wherein the buffer layer is comprised of a phthalocyanine derivative, and wherein the hole transport layer is comprised of a tertiary aromatic amine; an electroluminescent device wherein the tertiary aromatic amine is N,N'-di-1-naphthyl-N,N'-diphenyl-benzidine; an electroluminescent device wherein the electron transport layer is comprised of tri(8-hydroxyquinolinato)aluminum; an electroluminescent device wherein the electron transport layer is comprised of triazines, or a triazine; an electroluminescent device wherein the triazine is selected from the group consisting of 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3,5-triazinyl)]-1,1'-biphenyl, and 2,4,6-tri(1,1'-biphenyl-4-yl)-1,3,5-triazine; an electroluminescent device wherein the light emitting layer further includes a fluorescent dye; an electroluminescent device wherein the fluorescent dye is selected from the group consisting of 9-acridones, quinacridones, and perylenes; an electroluminescent device wherein the light emitting layer is comprised of a mixture of hydrocarbon compounds of Formulas (I), (II), or mixtures thereof, and wherein the second hydrocarbon (II) is present in an amount of from about 1 to about 50 mole percent based on the mole percent of the first hydrocarbon compound, and wherein the total of (I) and (II) is about 100 percent; an electroluminescent device wherein the anode is comprised of indium tin oxide in a thickness of from about 1 to about 500 nanometers; the buffer layer is comprised of a phthalocyanine in a thickness of from about 5 to about 80 nanometers, the hole transport layer is comprised of a tertiary aromatic amine in a thickness of from about 5 to about 300 nanometers; the light emitting hydrocarbon layer is of a thickness of about 5 to about 300 nanometers, and the cathode is comprised of a magnesium silver alloy or a lithium aluminum alloy in a thickness of from about 10 to about 800 nanometers; an electroluminescent device wherein the element is a layer, the first electrode is an anode, and the second electrode is a cathode; an electroluminescent device wherein the element is comprised of a layered electroluminescent arrangement comprised of a hole transport layer, and a light emitting layer wherein optionally hydrocarbon compounds are added thereto, and an electron transport layer; and which element is positioned in between the anode and cathode; an electroluminescent device wherein the element represents a single layer, a plurality of layers, or a plurality of laminated layers; an electroluminescent device wherein the electron transport layer is comprised of tri(8-hydroxyquinolinato)aluminum, or a triazine; an electroluminescent device wherein the light emitting layer further includes a fluorescent dye; an electroluminescent device and further including an electron transport layer wherein the hole transport layer is comprised of a tertiary aromatic amine; an electroluminescent device wherein the first electrode is an anode of indium tin oxide, the hole transport is a tertiary aromatic amine, the light emitting hydrocarbon is of a thickness of from about 5 to about 300 nanometers, and the second electrode is a cathode of a metal alloy; a compound of Formulas (I), (II), or mixtures thereof; a compound of the Formulas

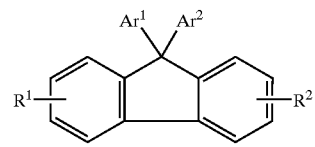

(I)

wherein $R^1$ and $R^2$ are substituents, which are selected from the group consisting of hydrogen, an alkyl, an alicyclic alkyl, an alkoxy, a halogen, and a cyano; $Ar^1$ and $Ar^2$ are each independently an aromatic component or an aryl group comprised of a from about 4 to about 15 conjugate-bonded or fused benzene rings; or

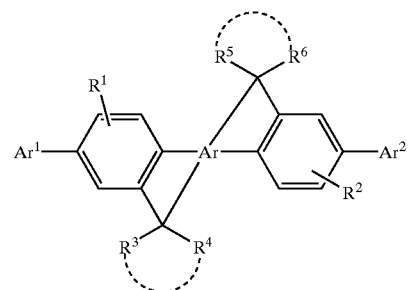

(II)

wherein $R^1$ and $R^2$ are independently selected from the group consisting of hydrogen, an alkyl group, an alicyclic alkyl group, an aryl group, an alkoxy group, a halogen, a cyano group; $R^3$, $R^4$, $R^5$, and $R^6$ are independently selected from the group consisting of hydrogen, an alkyl group, an alicyclic alkyl group, an aryl group, and an alkoxy group; wherein $R^3$ and $R^4$, or $R^4$ and $R^5$ are optionally combined into a bivalent hydrocarbon group selected from the group consisting of an alkylene, an alkylidene, an alicyclic alkylidene, and an arylalkylidene; wherein $Ar^1$ and $Ar^2$ are independently an aryl group; and wherein Ar is a tetravalent aromatic group; an organic electroluminescent device wherein the first electrode is an anode and the second electrode is a cathode.

Illustrative examples of the hydrocarbon compounds encompassed by Formula (I) include the following Compound (I-1)

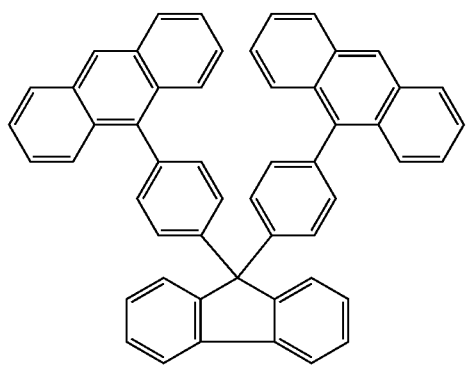

Compound (I-2)

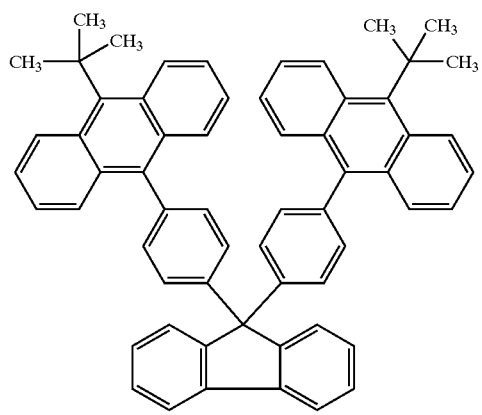

-continued
Compound (I-3)
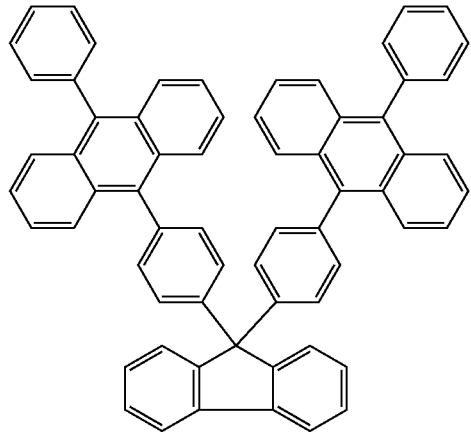
Compound (I-4)
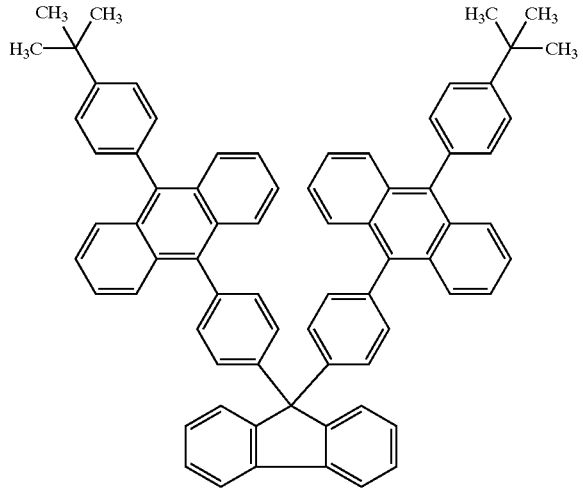
Compound (I-5)
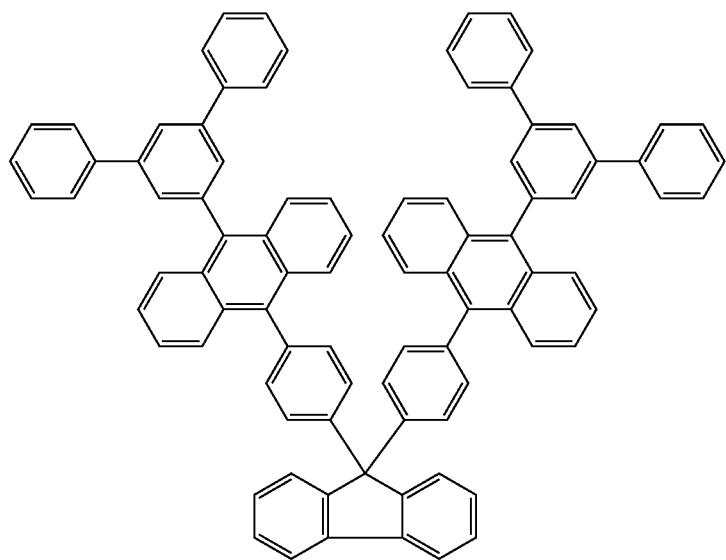

-continued
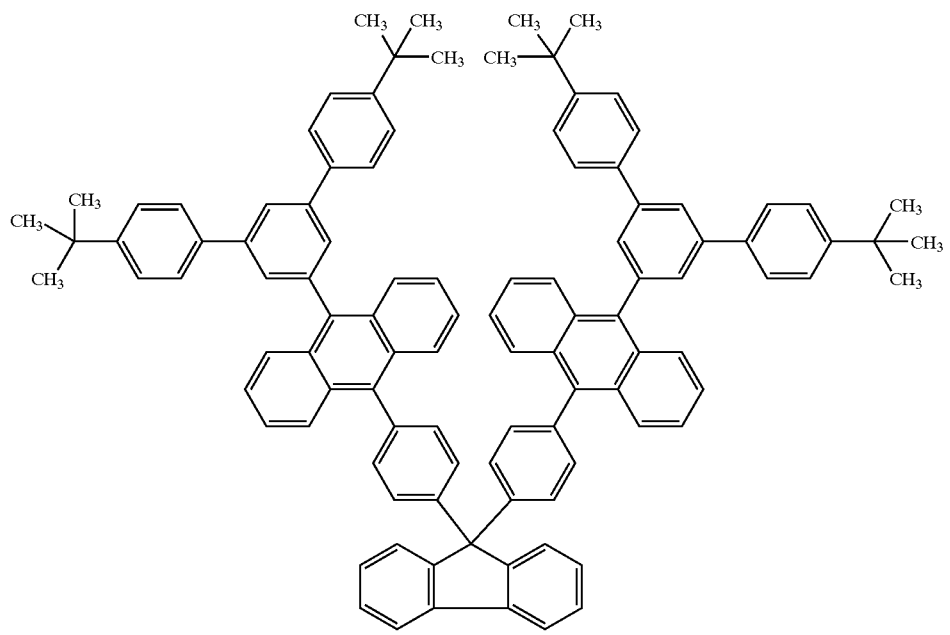
Compound (I-6)
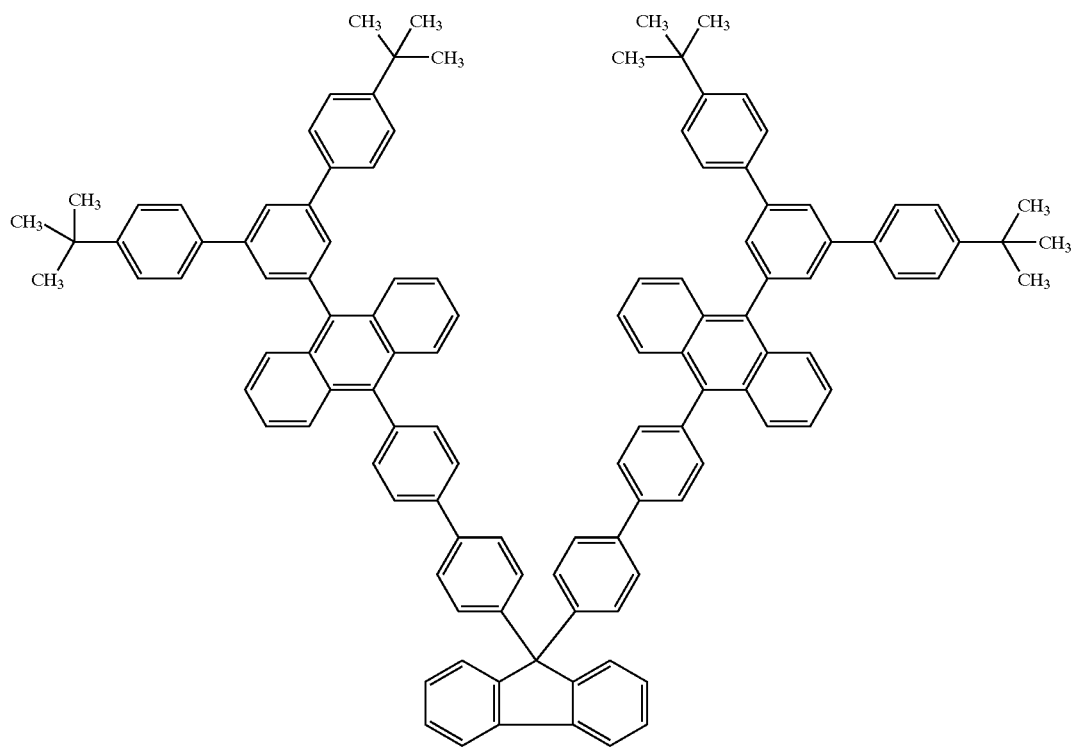
Compound (I-7)

-continued

Compound (I-8)
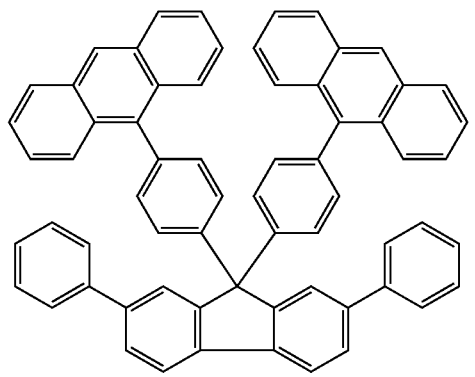

Compound (I-9)
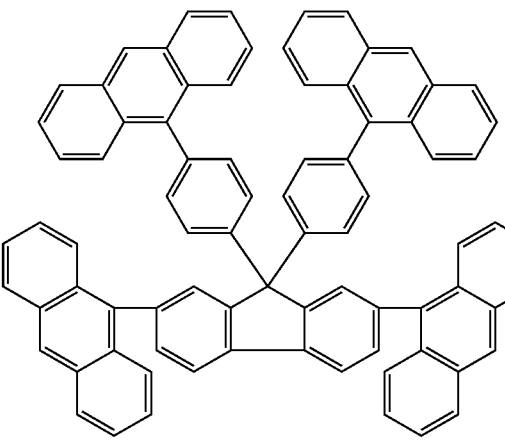

Compound (I-10)
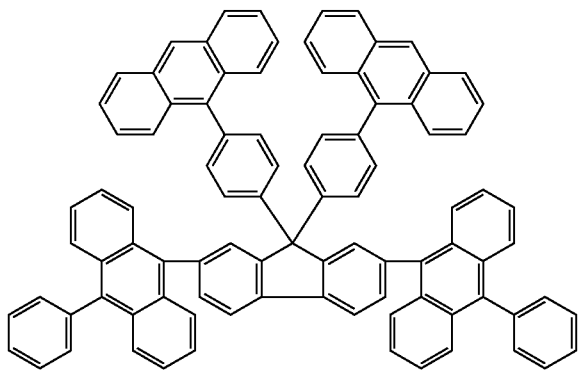

Compound (I-11)
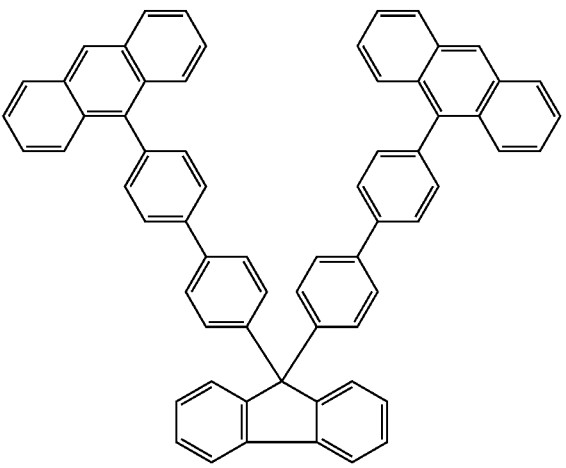

The present invention also relates to an organic electroluminescent device comprised of an anode and a cathode, and an EL element positioned between the anode and the cathode, wherein said EL element has at least one light emitting layer containing a luminescent hydrocarbon compound comprised of the Formula (II)

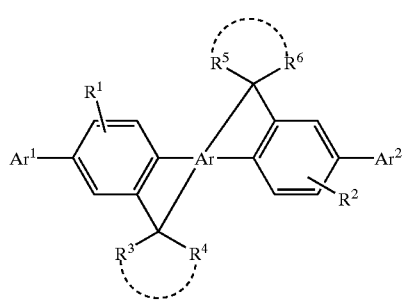

(II)

wherein $R^1$ and $R^2$ are substituents, which may be selected from the group consisting of hydrogen, an alkyl group with, for example, from 1 to about 6 carbon atoms, an alicyclic alkyl group with from about 3 to about 15 carbon atoms, an aryl group with about 6 to about 30 carbon atoms, an alkoxy group with preferably from 1 to about 6 carbon atoms, a halogen, a cyano group and the like; illustrative examples of alkyl group are methyl, ethyl, tert-butyl and the like. Illustrative examples of alicyclic alkyl group are cyclopentyl, cyclohexyl, 4-tert-butylcyclohexyl, and the like; examples of aryl for $R^1$ and $R^2$ include a phenyl, a tolyl, 4-tert-butylphenyl, and the like; typical examples of alkoxy group include methoxy, ethoxy, isopropoxy, tert-butoxy, and the like. $R^3$, $R^4$, $R^5$, and $R^6$ are each a substituent, which may be selected from the group consisting of hydrogen, an alkyl group with, for example, from 1 to about 6 carbon atoms, an alicyclic alkyl group with from about 3 to about 15 carbon atoms, an aryl group with about 6 to about 30 carbon atoms, an alkoxy group with preferably from 1 to about 6 carbon atoms, and the like. Illustrative examples of substituents include hydrogen, methyl, ethyl, tert-butyl, cyclopentyl, cyclohexyl, 4-tert-butylcyclohexyl, a phenyl, a tolyl, 4-tert-butylphenyl, 4-methoxyphenyl, methoxy, ethoxy, propoxy, butoxy, and the like. $R^3$ and $R^4$, or $R^4$ and $R^5$ may combined into a bivalent hydrocarbon group being selected from, for example, the group consisting of an alkylene group with from about 3 to about 8 carbon atoms, an alkylidene group with from about 3 to about 15 carbon atoms, an alicyclic alkylidene group with from about 3 to about 15 carbon atoms, and an arylalkylidene group with from about 6 to about 30 carbon atoms, and the like. Illustrative examples of bivalent group for $R^3$ and $R^4$, or $R^4$ and $R^5$ include 1,5-pentylene, 1,6-hexalene, ethylidene, phenylmethylidene, diphenylmethylidene, cyclohexalidene, 4-tert-butylcyclohexalidene, and the like.

Ar¹ and Ar² are each an aromatic component, such as an aryl group with from about 6 to about 30 carbon atoms, or an arylvinyl group with from about 6 to about 30 carbon atoms, which may, for example, be selected from the group consisting of a phenyl, a biphenylyl, a 3,5-diarylphenyl, a phenylvinyl, a diphenylvinyl, and the like. Illustrative examples of aryl groups for Ar¹ and Ar² are a phenyl, p-tert-butylphenyl, p-methoxyphenyl, 3,5-diphenylphenyl, 3,5-bis(p-tert-butylphenyl)phenyl, biphenylyl, 4'-methoxybiphenyl-4-yl, 2-phenylvinyl, 2,2-diphenylvinyl, and the like.

Ar for Formula (II) is in embodiments a tetravalent aromatic group with, for example, from about 6 to about 60 carbon atoms, and which group may be selected, for example, from the group consisting of

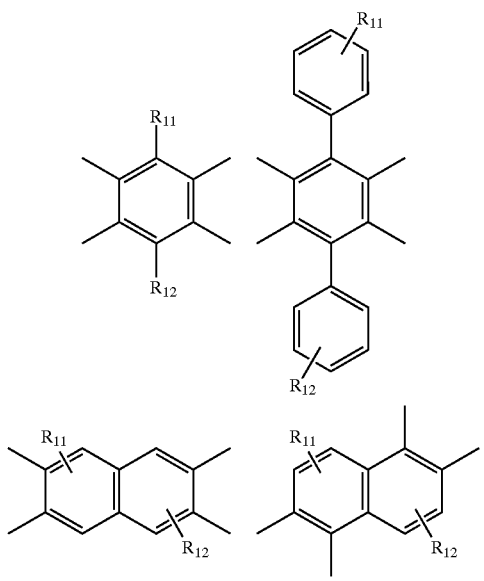

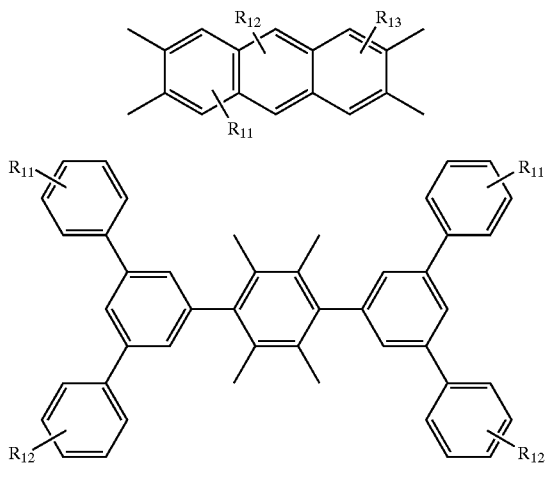

wherein $R_{11}$, $R_{12}$, and $R_{13}$ are each a substituent, which may be selected from the group consisting of hydrogen, an alkyl group with, for example, from 1 to about 6 carbon atoms, an alicyclic alkyl group with, for example, from about 3 to about 15 carbon atoms, an alkoxy group with, for example, from about 1 to about 6 carbon atoms, a dialkylamino group with from about 1 to about 3 carbon atoms, a halogen, a cyano group and the like. Illustrative examples of substituents for $R_{11}$, $R_{12}$, $R_{13}$ include hydrogen, methyl, tert-butyl, cyclohexyl, methoxy, tert-butoxy, fluorine, cyano and the like.

Examples of specific hydrocarbon compounds illustrated by Formula (II) include

Compound (II-1)

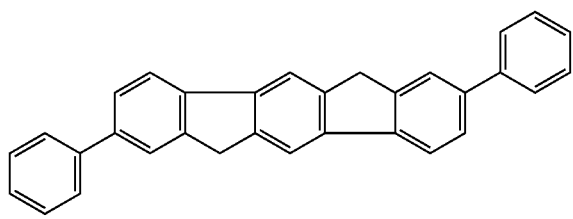

Compound (II-2)

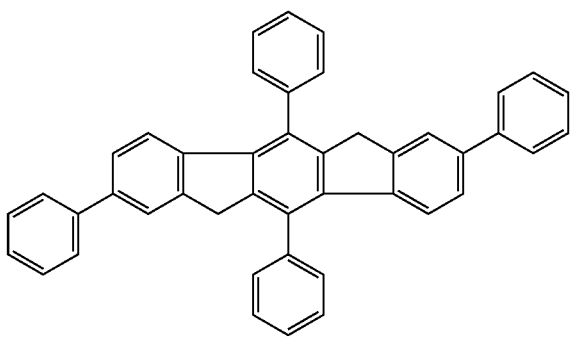

-continued
Compound (II-3)
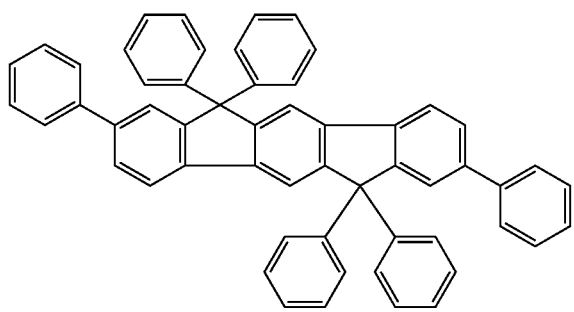
Compound (II-4)
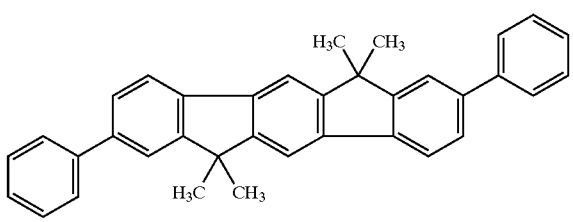
Compound (II-5)
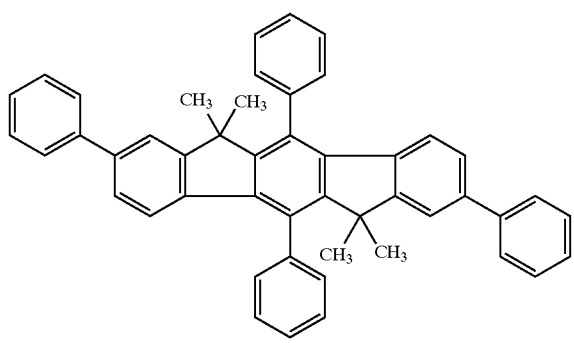
Compound (II-6)
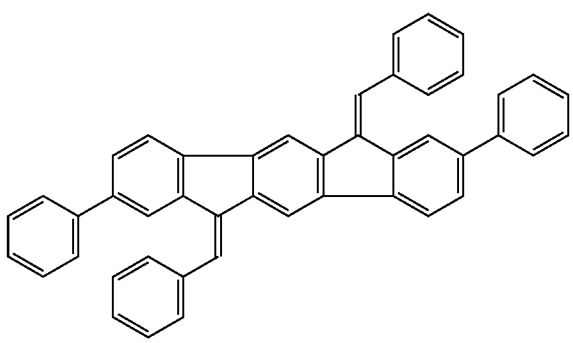
Compound (II-7)
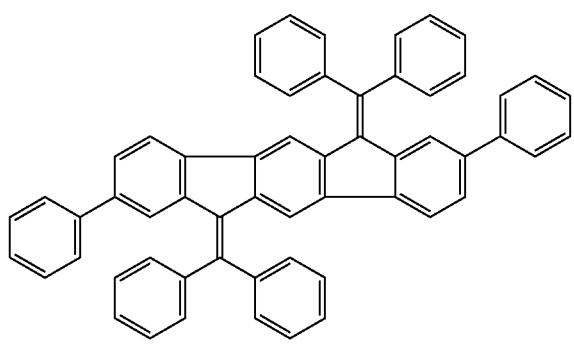
Compound (II-8)
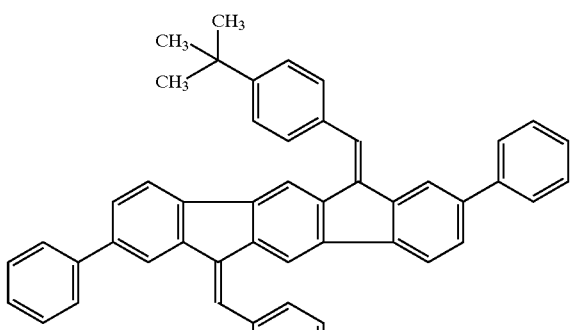
Compound (II-9)
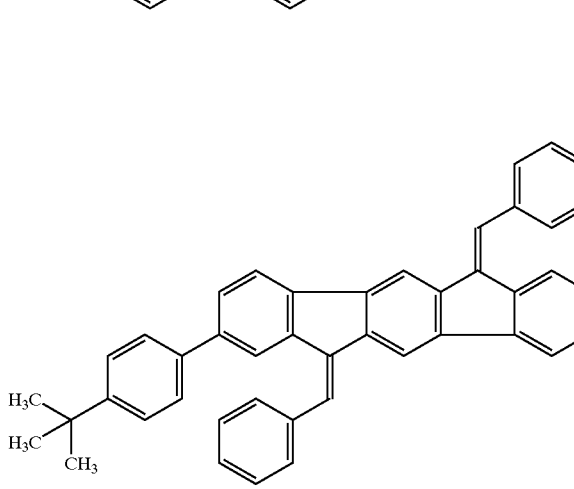

-continued
Compound (II-10)
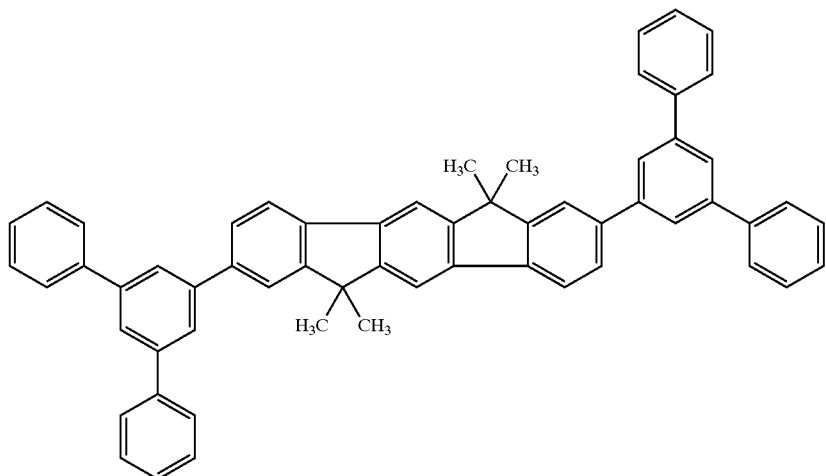
Compound (II-11)
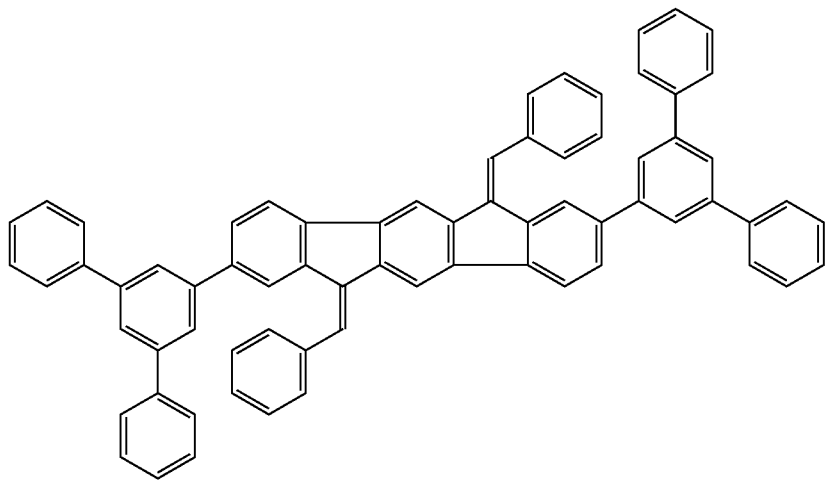
Compound (II-12)
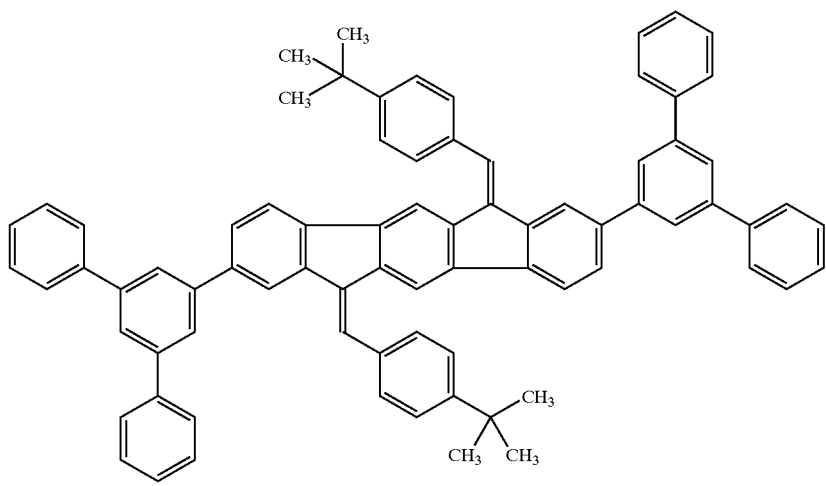

Compound (II-13)
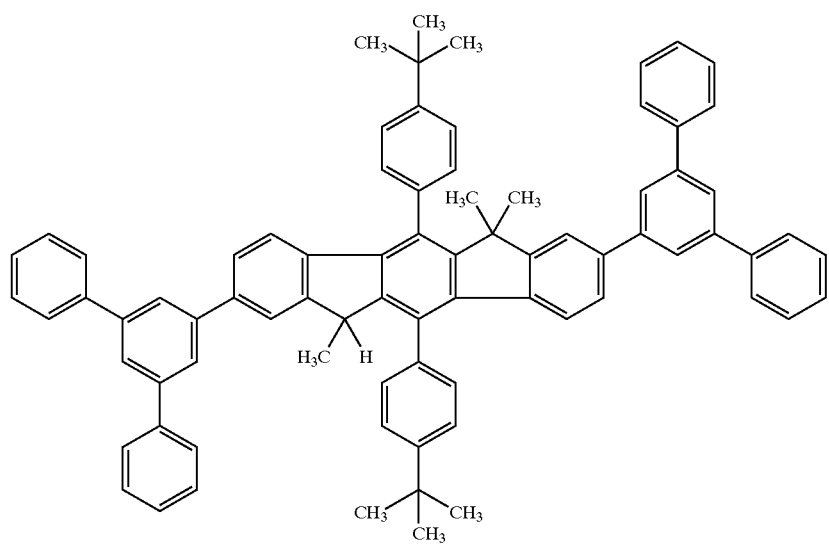
Compound (II-14)
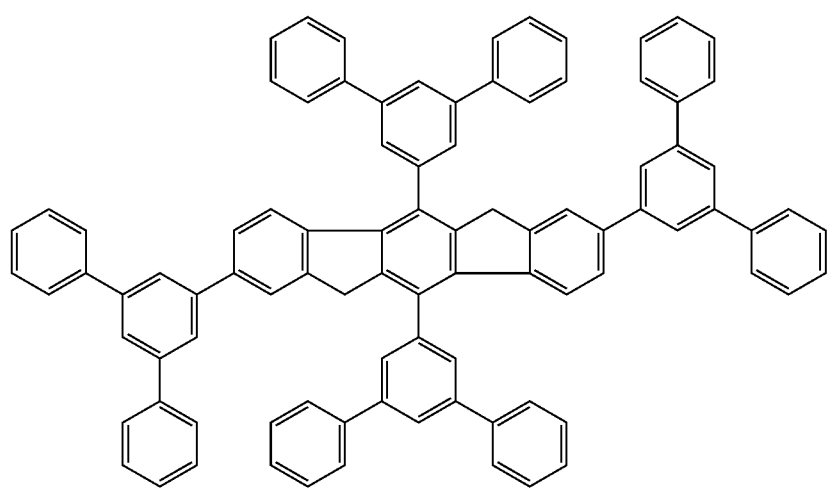
Compound (II-15)
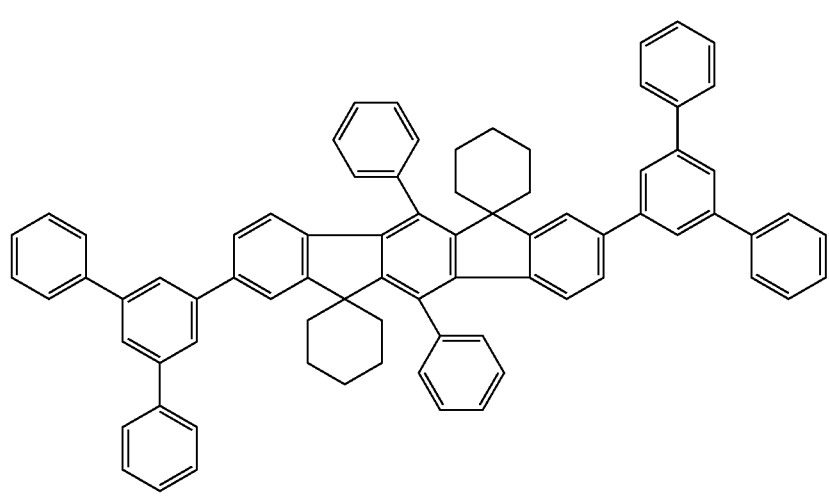

-continued
Compound (II-16)
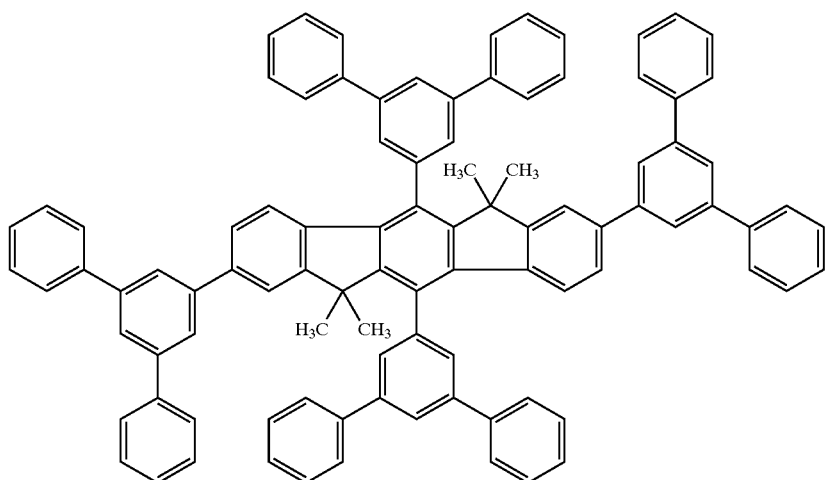
Compound (II-17)
Compound (II-18)
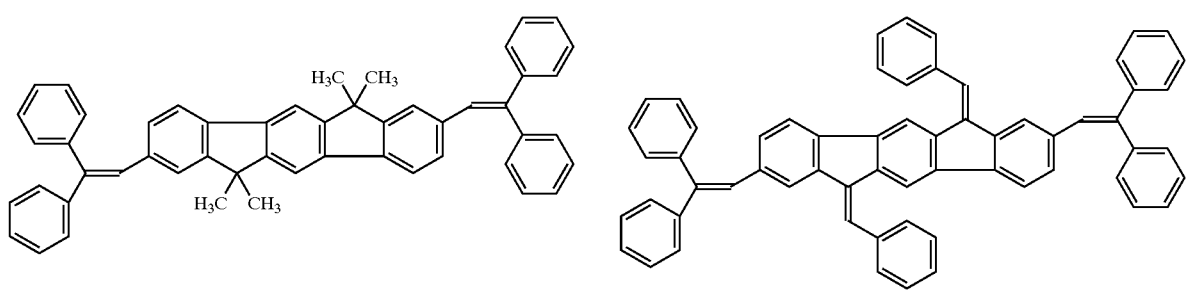
Compound (II-19)
Compound (II-20)
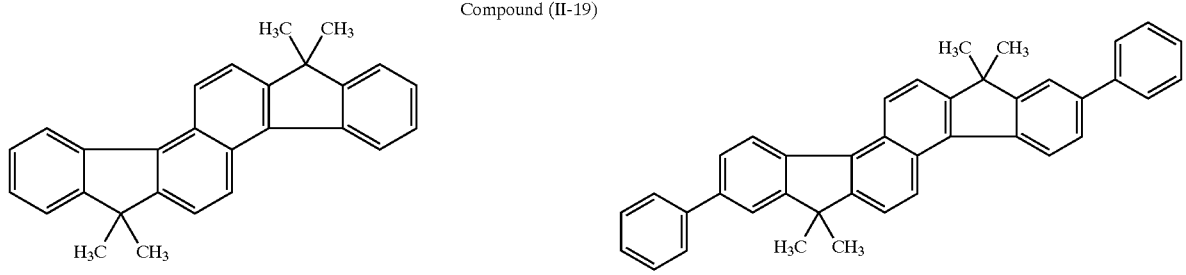
Compound (II-21)
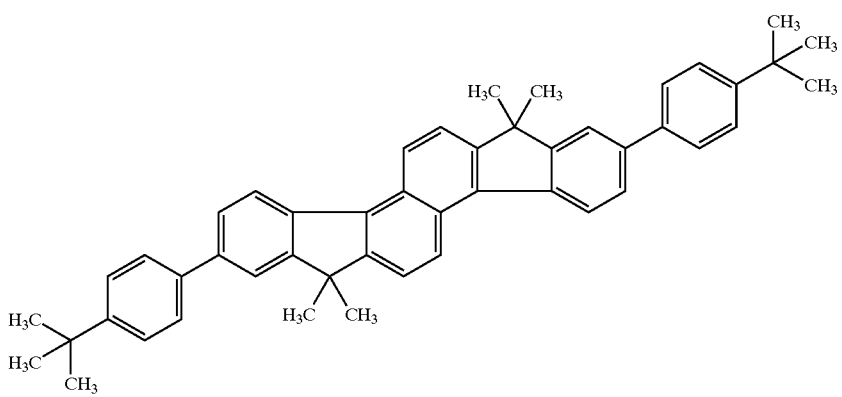

Compound (II-22)

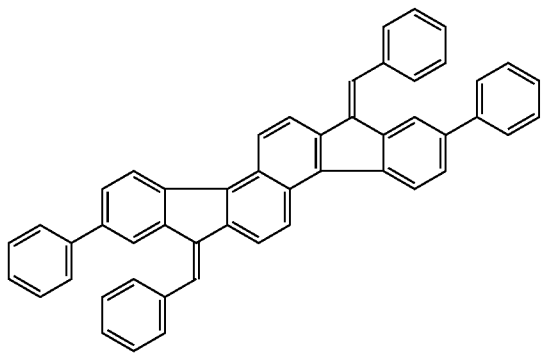

Compound (II-23)

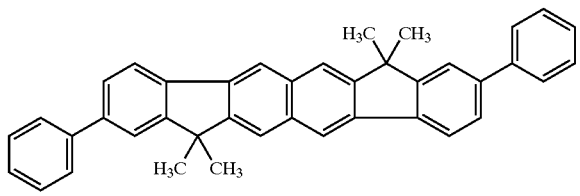

Compound (II-24)

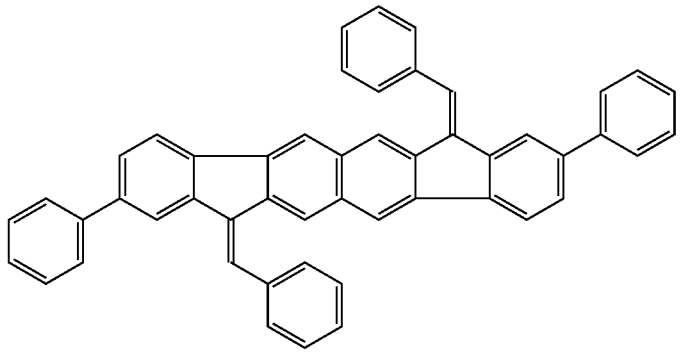

The hydrocarbon compounds may be generated by a number of synthetic processes. For example, they can be synthesized as follows: a mixture consisting of one equivalent of a suitable dibromoarene compound or an arene ditriflate compound, such as 4,4'-(9-fluorenylidene)diphenyl ditriflate, two equivalents of a base, such as potassium carbonate, two equivalents of an arene diborate compound, such as 9-anthryl-4,4,5,5-tetramethyl-1,3,2-dioxaborolane, 0.01 equivalent of a palladium catalyst, such as tetrakis(triphenylphosphine)palladium, and suitable amounts of an inert solvent, such as dioxane, is heated under argon to reflux for a suitable time, about 48 hours. After cooling to room temperature, about 23° C., the reaction contents are added into methanol or water, and the precipitate is collected by filtration. The product may further be purified by standard purification means including recrystallization and sublimation. The hydrocarbon compounds thus obtained may be confirmed by elemental analysis, NMR or IR spectrometric identification techniques.

The luminescent hydrocarbon materials described herein exhibit strong fluorescence in the solid state in the region from about 400 nanometers to, for example, about 600 nanometers. They have the ability of forming thin films with excellent thermal stability by vacuum evaporation.

In embodiments, the light emitting layer 5 disclosed herein may further include a fluorescent material, wherein the layer is formed of a luminescent composition comprised of a hydrocarbon compound illustrated by Formulas through (I) or (II) as a host component and a guest fluorescent material. By mixing with the hydrocarbon host component a small amount of a fluorescent material capable of emitting light in response to hole-electron recombination, improved device performance characteristics, such as emission hue and electroluminescent efficiency, may be achieved. The fluorescent material is present in an amount of, for example, from about 0.01 to about 10 weight percent, or from about $10^{-3}$ to about 10 mole percent, based on the moles of the hydrocarbon host material, and preferably from about 1 to about 5 weight percent of the host hydrocarbon component. Suitable fluorescent material employed as the guest component are those possessing, for example, a bandgap no greater than that of said host component and a potential less negative than that of the host component. The fluorescent materials can be blended with the host hydrocarbon material to form a common phase.

Illustrative examples of fluorescent materials are dyes selected, for example, from the group consisting of coumarin, dicyanomethylene pyranes, polymethine, oxabenzanthrane, xanthene, pyrylium, carbostyl, perylene, and the like; preferable examples of fluorescent materials include acridone dyes such as N-methyl-9-acridone, N-methyl-2-methoxy-9-acridone, N-methyl-2-phenoxy-9-acridone, N-methyl-2-t-butoxy-9-acridone, N-phenyl-2-methoxy-9-acridone, N-methyl-2-phenyl-9-acridone, N-methyl-2-diethylamino-9-acridone, and the like; a dye selected from the group consisting of quinacridone derivatives; illustrative examples of quinacridone dyes include of N,N'-dimethylquinacridone, N,N'-dimethyl-2-methyl quinacridone, N,N'-dimethyl-2,9-dimethylquinacridone, N,N'-dimethyl-2-chloroquinacridone, N,N'-dimethyl-2-fluoroquinacridone, and N,N'-dimethyl-1,2-benzoquinacridone, and the like. Also, another preferred class of fluorescent materials is fused ring fluorescent dyes. Examples of the fused ring fluorescent dyes include perylene, tetra-t-butylperylene, rubrene, anthracene, coronene, phenanthrecene, pyrene and the like, as illustrated in U.S. Pat. No. 3,172,862, the disclosure of which is totally incorporated herein by reference. Also, fluorescent materials that can be selected as a dopant include butadienes, such as 1,4-diphenylbutadiene, tetraphenylbutadiene, stilbenes, and the like, as illustrated in U.S. Pat. Nos. 4,356,429 and 5,516,577, the disclosures of which are totally incorporated herein by reference.

The light emitting layer herein may be formed by any convenient manner. For example, it can be prepared by vacuum deposition from the evaporation of the luminescent hydrocarbon compound, or from the simultaneous evaporation of the hydrocarbon host material and the fluorescent material. The thickness of the light emitting layer is not particularly limited, and can range from about 5 nanometers to about 300 nanometers, or from about 10 nanometers to about 100 nanometers.

It is desirable that the organic EL devices of the present invention comprise a supporting substrate. Illustrative examples of the supporting substrate include polymeric components, glass, and the like, and polyesters like MYLAR®, polycarbonates, polyacrylates, polymethacrylates, polysulfones, quartz, and the like. Other substrates can also be selected provided, for example, they can effectively support the other layers, and that it does not interfere with the device functional performance. The thickness of the substrate can be, for example, from about 25 to about 1,000 microns or more, and for example, from about 50 to about 500 microns depending, for example, on the structural demands of the device.

Examples of the anode, which is contiguous to the substrate, include positive charge injecting electrodes, such as indium tin oxide, tin oxide, gold, platinum, or other suitable materials, such as electrically conductive carbon, $\pi$-conjugated polymers such as polyaniline, polypyrrole, and the like with, for example, a work function equal to, or greater than about 4 electron volts, and more specifically, from about 4 to about 6 electron volts. The thickness of the anode can range from about 1 to about 5,000 nanometers with the preferred range being dictated by the optical constants of the anode material. One preferred range of thickness is from about 30 to about 100 nanometers.

The buffer layer is optional, and which layer primarily functions to achieve desirable charge injection of holes from the anode, and to improve the adhesion between the anode and the organic hole transporting layer, thus further improving the device operation stability. Specific examples of buffer layer materials include conductive materials, such as polyaniline and its acid-doped forms, polypyrrole, poly (phenylene vinylene), and known semiconductive organic materials; porphyrin derivatives disclosed in U.S. Pat. No. 4,356,429, such as 1,10,15,20-tetraphenyl-21H,23H-porphyrin copper (II); copper phthalocyanine, copper tetramethyl phthalocyanine; zinc phthalocyanine; titanium oxide phthalocyanine; magnesium phthalocyanine; and the like, the disclosures of each of these patents being totally incorporated herein by reference.

A class of hole transporting materials that can be selected for the buffer layer are the aromatic tertiary amines, such as those disclosed in U.S. Pat. No. 4,539,507, the disclosure of which is totally incorporated herein by reference. Representative examples of aromatic tertiary amines are bis(4-dimethylamino-2-methylphenyl)phenylmethane, N,N,N-tri(p-tolyl)amine, 1,1-bis(4-di-p-tolylaminophenyl) cyclohexane, 1,1-bis(4-di-p-tolylaminophenyl)-4-phenyl cyclohexane, N,N'-diphenyl-N,N'-bis(3-methylphenyl)-1,1'-biphenyl-4,4'-diamine, N,N'-diphenyl-N,N'-bis(3-methylphenyl)-1,1'-biphenyl-4,4'-diamine, N,N'-diphenyl-N,N'-bis(4-methoxyphenyl)-1,1'-biphenyl-4,4'-diamine, N,N,N',N'-tetra-p-tolyl-1,1'-biphenyl-4,4'-diamine, N,N'-di-1-naphthyl-N,N'-diphenyl-1,1'-biphenyl-4,4'-diamine, and the like. Another class of aromatic tertiary amines selected for the hole transporting layer is polynuclear aromatic amines, such as N,N-bis-[4'-(N-phenyl-N-m-tolylamino)-4-biphenylyl]aniline; N,N-bis-[4'-(N-phenyl-N-m-tolylamino)-4-biphenylyl]-m-toluidine; N,N-bis-[4'-(N-phenyl-N-m-tolylamino)-4-biphenylyl]-p-toluidine; N,N-bis-[4'-(N-phenyl-N-p-tolylamino)-4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-toluidine; N,N-bis-[4'-(N-phenyl-N-p-chlorophenylamino)-4-biphenylyl]-m-toluidine; N,N-bis-[4'-(N-phenyl-N-m-chlorophenylamino)-4-biphenylyl]-m-toluidine; N,N-bis-[4'-(N-phenyl-N-'m-chlorophenylamino)-4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)-4-biphenylyl]-m-chloroaniline; N,N-bis-[4'-(N-phenyl-N-m-tolylamino)-4-biphenylyl]-1-aminonaphthalene and the like.

The buffer layer comprised of aromatic tertiary amines described herein may further include, as disclosed in U.S. Pat. No. 5,846,666, the disclosure of which is totally incorporated herein by reference, a stabilizer comprised of certain hydrocarbon compounds, such as rubrene, 4,8-diphenylanthracene, and the like. The buffer layer can be prepared by forming a suitable compounds into thin film by known methods, such as vapor deposition or spin-coating. The thickness of buffer layer thus formed is not particularly limited, and can be in a range of from about 5 nanometers to about 300 nanometers, and preferably from about 10 nanometers to about 100 nanometers.

The hole transporting layers can be comprised of a hole transporting material with a thickness ranging, for example, from about 1 nanometer to about 200 nanometers, and preferably from about 5 nanometers to about 100 nanometers. This layer can reduce the driving voltage of the device and improve the confinement of the injected charge recombination within the hydrocarbon light emitting layer. Any conventional suitable aromatic amine hole transporting materials described for the buffer layer may be selected for forming this layer.

A preferred class of hole transporting materials selected for forming the hole transporting layer is comprised of N,N,N',N'-tetraarylbenzidine derivatives. Illustrative examples of benzidine derivatives include N,N'-diphenyl-N,N'-bis(3-methylphenyl)-1,1'-biphenyl-4,4'-diamine, N,N'-diphenyl-N,N'-bis(4-methoxyphenyl)-1,1'-biphenyl-4,4'-diamine, N,N,N',N'-tetra-p-tolyl-1,1'-biphenyl-4,4'-diamine, N,N'-1-naphthyl-N,N'-diphenyl-1,1'-biphenyl-4,4'-diamine and the like.

The electron optional transporting layer selected for the primary purpose of improving the electron injection characteristics and the emission uniformity of the EL devices of the present invention are of a suitable thickness, for example from about 1 nanometer to about 300 nanometers, or from about 5 nanometers to about 100 nanometers. Illustrative examples of electron transporting compounds, which can be utilized in this layer, include the metal chelates of 8-hydroxyquinoline as disclosed in U.S. Pat. Nos. 4,539,507; 5,151,629, and 5,150,006, the disclosures of which are totally incorporated herein by reference. Illustrative examples include tris(8-hydroxyquinolinate)aluminum, a preferred one, tris(8-hydroxyquinolinate)gallium, bis(8-hydroxyquinolinate)magnesium, bis(8-hydroxyquinolinate) zinc, tris(5-methyl-8-hydroxyquinolinate)aluminum, tris(7-propyl-8-quinolinolato)aluminum, bis[benzo{f}-8-quinolinate]zinc, bis(10-hydroxybenzo[h]quinolinate) beryllium, and the like. Another class of metal chelate compounds for electron transport layer is the oxadiazole metal chelates disclosed in U.S. Pat. No. 5,925,472, the disclosures of which are totally incorporated herein by reference.

Another class of electron transport materials comprises triazine compounds as disclosed in U.S. Pat. No. 6,057,048, the disclosure of which is totally incorporated herein by reference. Illustrative specific examples include 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-anisyl-1,3,5-triazinyl)]-1,1'-biphenyl, 4,4'-bis-[2-(4-β-naphthyl-6-phenyl-1,3,5-triazinyl)]-1,1'-biphenyl, 4,4'-bis-[2-(4,6-di-biphenylyl-1,3,5-triazinyl)]-1,1'-biphenyl, 4,4'-bis-[2-(4,6-di-phenyl-1,3,5-triazinyl)]-2,2'-dimethyl-1,1'-biphenyl, 4,4'-bis-[2-(4,6-di-phenyl-1,3,5-triazinyl)]-stilbene, 4,4'-bis-[2-(4-phenyl-6-p-tolyl-1,3,5-triazinyl)]-stilbene, 2,4,6-tri(4-biphenylyl)-1,3,5-triazine, and the like.

The cathode can be comprised of any metal, including high, for example from about 4.0 eV to about 6.0 eV, or low work function component, such as metals with, for example, an eV of from about 2.5 eV to about 4.0 eV (electron volts). The cathode can be derived from a combination of a low work function metal (less than about 4 eV) and at least one other metal. Effective proportions of the low work function metal to the second or other metal are from less than about 0.1 percent to about 99.9 percent by weight. Illustrative examples of low work function metals include alkaline metals such as lithium or sodium, Group 2A or alkaline earth metals such as beryllium, magnesium, calcium, or barium, and Group III metals including rare earth metals and the actinide group metals such as scandium, yttrium, lanthanum, cerium, europium, terbium, or actinium. Lithium, magnesium and calcium are preferred low work function metals.

The thickness of cathode ranges from, for example, about 10 nanometers to about 500 nanometers. The Mg:Ag cathodes of U.S. Pat. No. 4,885,211, the disclosure of which constitutes one preferred cathode, can be selected for the EL devices of the present invention. Another cathode construction is described in U.S. Pat. No. 5,429,884, the disclosure of which are totally incorporated herein by reference, wherein the cathodes are, for example, formed from lithium alloys with other high work function metals such as aluminum and indium.

Both the anode and cathode of the EL devices of the present invention may contain a protective coating thereon, and the anode and cathode can be of any convenient forms. A thin conductive layer can be coated onto a light transmissive substrate, for example a transparent or substantially transparent glass plate or plastic film. The EL device can include a light transmissive anode formed from tin oxide or indium tin oxide coated on a glass plate. Also, very thin, for example less than about 200 Å, and more specifically, from about 75 to about 150 Angstroms, light-transparent metallic anodes can be used, such as gold, palladium, and the like. In addition, transparent or semitransparent thin layers, for example from 50 to about 175 Angstroms of conductive carbon or conjugated polymers such as polyaniline, polypyrrole, and the like can be used as anodes. Any suitable light transmissive polymeric film can be employed as the substrate. Additional suitable forms of the anode 3 and cathode 6 are illustrated in U.S. Pat. No. 4,885,211.

Aromatic refers, for example, to aryl, such as phenyl, and which aryl can contain, for example, from about 6 to about 72 carbon atoms; aliphatic refers, for example, to aklyl, and alkoxy, each with from about 1 to about 40, preferably about 25, and most preferably from about 1 to about 6 carbon atoms; halogen refers, for example, to chloride, bromide, fluoride or iodide, and n is from about zero (0) to about 3.

The following Examples are provided to further illustrate various species of the present invention, it being noted that these Examples are intended to illustrate and not limit the scope of the present invention.

EXAMPLE I

Synthesis of 9-anthryl-4,4,5,5-tetramethyl-1,3,2-dioxaborolane

To a solution of 9-bromoanthracene (9.73 grams) in 100 milliliters of anhydrous diethyl ether were slowly added at about 0° C. 23 milliliters of 2M n-butyllithium hexane solution. After the addition, the reaction mixture was warmed to room temperature (about 23° C.) for 30 minutes. The resulting mixture was then cooled to around −30° C. and 2-isopropoxy-4,4,5,5-tetramethyl-1,3,3-dioxaborolane (9.27 milliliters) was added through a syringe. The resulting reaction mixture was warmed to room temperature (about 23° C.), and stirred overnight (about 18 hours throughout). After being diluted with 50 milliliters of hexane, the mixture resulting was filtered through celite. Removal of the solvents under reduced pressure yielded a yellowish solid (6.70 grams) which contains more than 90 percent of 9-anthryl-4,4,5,5-tetramethyl-1,3,2-dioxaborolane. The product may be used without further purification. This compound and its structure was confirmed by proton NMR analysis.

EXAMPLE II

Synthesis of 4,4'-(9-fluorenylidene)diphenyl Ditriflate

To a solution of 4,4'-(9-fluorenyledene)diphenol (10 grams) in 100 milliliters of anhydrous pyridine were added at about 5° C. grams 11 milliliters of triflic acid anhydride. After the addition, the reaction mixture was warmed to room temperature (about 23° C.) for 6 hours. After removal of the pyridine under reduced pressure, the residue was dissolved in 200 milliliters of dichloromethane, washed with 5 percent HCl aqueous solution, followed by washing with water. After removal of the solvents, the resulting crude residue was purified through a silica column to yield 17.26 grams of 4,4'-(9-fluorenylidene)diphenyl ditriflate. This compound and its structure was confirmed by proton NMR analysis.

EXAMPLE III

Synthesis of 9,9-bis[4-(9-anthryl)phenyl) fluorene

A mixture of 9-anthryl-4,4,5,5-tetramethyl-1,3,2-dioxaborolane (5 grams), 4,4'-(9-fluorenylidene)diphenyl ditriflate (5.3 grams), potassium carbonate (2.27 grams) in 50 milliliters of dioxane was purged with argon for 10 minutes. To this mixture was then added tetrakis (triphenylphosphine) palladium (0.37 gram). The reaction mixture was stirred at reflux for 48 hours under argon. After cooling to room temperature (about 23° C.), the mixture was diluted with 30 milliliters of methanol, and the precipitates were collected by filtration, washed with 5 percent HCl aqueous solution, followed by water to remove inorganic salts. After drying, the filtrates were purified by sublimation to yield 2.5 grams of 9,9-bis[4-(9-anthryl)phenyl) fluorene. This compound had a melting point of 425° C. The structure of this compound was confirmed by proton NMR and elemental analysis.

EXAMPLE IV

Synthesis of 10-bromo-9-phenylanthracene

To a solution of 9-phenylanthracene (10 grams) and ferric chloride (0.065 gram) in 100 milliliters of dichloromethane were added 6.70 grams of bromine in 30 milliliters of dichloromethane through an addition funnel at room temperature. The reaction mixture was stirred for 3 hours, and then washed with aqueous sodium thiosulfate and water. After removal of the solvents, the crude residue was recrystallized from ethanol to yield 12.5 grams of 10-bromo-9-phenylanthracene. The structure of this compound was confirmed by proton NMR analysis.

EXAMPLE V

Synthesis of 9-(10-phenylanthryl)-4,4,5,5-tetramethyl-1,3,2-dioxaborolane

To a solution of 10-bromo-9-phenylanthracene (8.69 grams) in 100 milliliters of anhydrous diethyl ether were slowly added at about 0° C. 16 milliliters of 2M n-butyllithium hexane solution. After the addition, the reaction mixture was warmed to room temperature (about 23° C.) for 30 minutes. The resulted mixture was then cooled to around –30° C. and 2-isopropoxy-4,4,5,5-tetramethyl-1,3,3-dioxaborolane (6.49 milliliters) was added through a syringe. The reaction mixture was warmed to room temperature (about 23° C.), and stirred overnight, about 18 hours. After being diluted with 50 milliliters of hexane, the mixture was filtered through celite. Removal of the solvents under reduced pressure yielded a yellowish solid (7.90 grams) which contains more than 90 percent of 9-(10-phenylanthryl)-4,4,5,5-tetramethyl-1,3,2-dioxaborolane. The product may be used without further purification. The structure of this compound was confirmed by proton NMR analysis.

EXAMPLE VI

Synthesis of 9.9-bis[4-(10-phenyl-9-anthryl)phenyl] fluorene

A mixture of 9-(10-phenylanthryl)-4,4,5,5-tetramethyl-1,3,2-dioxaborolane (3.8 grams), 4,4'-(9-fluorenylidene)diphenyl ditriflate (3.23 grams), potassium carbonate (1.38 grams) in 50 milliliters of dioxane was purged with argon for 10 minutes. To this mixture was then added tetrakis(triphenylphosphine)palladium (0.23 gram). The reaction mixture was stirred at reflux for 48 hours under argon. After cooling to room temperature (about 23° C.), the mixture was diluted with 30 milliliters of methanol, and the precipitates were collected by filtration, washed with 5 percent HCl aqueous solution followed by washing with water to remove inorganic salts. After drying, the filtrates were purified by sublimation to yield 1.5 grams of 9,9-bis[4-(9-anthryl) phenyl) fluorene, with a melting point of 518° C. The structure of this compound was confirmed by proton NMR and elemental analysis.

EXAMPLE VII

Synthesis of 6,6,12,12-tetramethyl-2,8-diphenylindeno[1,2b]fluorene

This compound may be prepared in accordance to the procedure described in *J. Org. Chem.*, Vol. 56, 1210 (1991) (2,8-diphenyl-6,12-dihydroindeno[1,2b]fluorene, followed by methylation).

EXAMPLE VIII

Organic EL devices comprising a light emitting layer of a fluorescent hydrocarbon compound of Formulas I, II or mixtures thereof, and more specifically, with the hydrocarbon of Example III can be fabricated in the following manner:

1. A 500 Å indium tin oxide (ITO) anode coated glass substrate was selected, the thickness of the glass substrate being about 1 millimeter. The glass was cleaned with a commercial detergent, rinsed with deionized water and dried in a vacuum oven at 60° C. for 1 hour. Immediately before use, the glass was treated with UV ozone for 0.5 hour.
2. The ITO anode coated on the glass substrate was then placed in a vacuum deposition chamber, and a buffer layer was applied. The buffer layer deposition rate and layer thickness were controlled by an Inficon Model IC/5 controller. Under a pressure of about $5 \times 10^{-6}$ Torr, a 15 nanometers thick buffer layer was deposited on the ITO glass substrate through evaporation of copper (II) phthalocyanine at a rate of 0.6 nanometer/second from a tantalum boat.
3. Onto the buffer layer, a 20 nanometers thick hole transport layer of N,N'-1-naphthyl-N,N'-diphenyl-1,1'-biphenyl-4,4'-diamine was deposited at a rate of 0.6 nanometer/second.
4. Onto the hole transport layer was deposited by evaporation a 40 nanometers light emitting layer of 9,9-bis[4-(9-anthryl)phenyl)fluorene at a rate of 0.6 nanometer/second.
5. A 20 nanometers thick electron transport layer of 4,4'-bis-[2-(4,6-diphenyl-1,3,5-triazinyl)]-1,1'-biphenyl was then deposited by evaporation at a rate of 0.6 nanometer/second onto the light emitting layer.
6. A 100 nanometer cathode of a magnesium silver alloy was deposited at a total deposition rate of 0.5 nanometer/second onto the light emitting layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The EL device as prepared above were retained in a dry box which was continuously purged with nitrogen gas; their performance thereof was assessed by measuring the current-voltage characteristics and light output under a direct current measurement. The current-voltage characteristics were determined with a Keithley Model 238 High Current Source Measure Unit. The ITO electrode was always connected to the positive terminal of the current source. At the same time, the light output from the device was monitored by a silicon photodiode.

The light output from this device was 350 cd/m$^2$ when it was driven by a direct current of 25 mA/cm$^2$. The device emitted a blue emission with CIE color coordinates of X=0.158 and Y=0.151 measured by Minolta Chromameter CS-100.

EXAMPLE IX

This organic EL device utilizes an electron transport layer comprised of a triazine and tri(8-hydroxyquinolinato) aluminum. The primary purpose of using triazine herein is to improve the chromaticity coordinates of blue emission color. The device can be fabricated in the following manner:

1. A 500 Å indium tin oxide (ITO) anode coated glass substrate was selected, the thickness of the glass substrate being about 1 millimeter. The glass was cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber, and a hole transport layer was applied. The hole transport layer deposition rate and layer thickness were controlled by an Inficon Model IC/5 controller. Under a pressure of about $5 \times 10^{-6}$ Torr, a 30 nanometers thick hole transport layer of N,N'-1-naphthyl-N,N'-diphenyl-1,1'-biphenyl-4,4'-diamine was deposited at a rate of 0.6 nanometer/second from a tantalum boat.

3. Onto the hole transport layer was deposited a 40 nanometers light emitting layer of 9,9-bis[4-(9-anthryl)phenyl]fluorene at a rate of 0.6 nanometer/second.

4. A total 30 nanometers thick electron transport layer was deposited onto the light emitting layer through first evaporation of a 10 nanometers thick layer of tris(1,1'-biphenyl-4-yl)-1,3,5-triazine at a rate of 0.6 nanometer/second, followed by evaporation of a 20 nanometers thick layer of tri(8-hydroxyquinolinato)aluminum at the same rate.

5. A 100 nanometer cathode of a magnesium silver alloy was deposited at a total deposition rate of 0.5 nanometer/second onto the light emitting layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The light output from this device was 380 cd/m$^2$ when it was driven by a direct current of 25 mA/cm$^2$. The device emitted a blue emission with CIE color coordinates of X=0.156 and Y=0.140 measured by Minolta Chromameter CS-100.

EXAMPLES X TO XIII

These Examples illustrated organic EL devices containing a light emitting layer comprised of a hydrocarbon host material and a fluorescent guest material. The devices were fabricated in the following manner:

1. A 500 Å indium tin oxide (ITO) anode coated glass substrate was selected, the thickness of the glass substrate being about 1 millimeter. The glass cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber, and a hole transport layer was applied. The hole transport layer deposition rate and layer thickness were controlled by an Inficon Model IC/5 controller. Under a pressure of about $5 \times 10^{-6}$ Torr, a 30 nanometers thick hole transport layer was deposited on the ITO glass substrate through evaporation of N,N'-1-naphthyl-N,N'-diphenyl-1,1'-biphenyl-4,4'-diamine at a rate of 0.6 nanometer/second from a tantalum boat.

3. Onto the hole transport layer were deposited a 42 nanometers thick light emitting layer through simultaneous evaporation from two independently controlled tantalum boats of 9,9-bis[4-(9-anthryl)phenyl]fluorene at a rate of 0.6 nanometer/second, and N-methyl-2-methoxy-9-acridone at such a rate that 1.6 weight percent or parts of this dye was doped.

4. A total 30 nanometers thick electron transport layer was deposited onto the light emitting layer through first evaporation of a 10 nanometers thick layer of tris(1,1'-biphenyl-4-yl)-1,3,5-triazine at a rate of 0.6 nanometer/second, followed by evaporation of a 20 nanometers thick layer of tri(8-hydroxyquinolinato)aluminum at the same rate.

5. A 100 nanometer cathode of a magnesium silver alloy was deposited at a total deposition. rate of 0.5 nanometer/second onto the light emitting layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The light output and CIE color coordinates from these devices were measured at a direct current of 25 mA/cm$^2$. The results are shown in the following Table.

| Example | Dopant (percent) | Light output (cd/m$^2$) (25 mA/cm$^2$) | CIE (X, Y) |
|---|---|---|---|
| X | 0 | 350 | 0.159, 0.147 |
| XI | 0.27 | 414 | 0.155, 0.133 |
| XII | 0.8 | 395 | 0.152, 0.122 |
| XIII | 1.6 | 373 | 0.150, 0.112 |

EXAMPLE XIV

This EL device was fabricated in accordance with, that is repeating the process of Example VIII except that 9,9-bis[4-(10-phenyl-9-anthryl)phenyl]fluorene was used in place of 9,9-bis[4-(9-anthryl)phenyl]fluorene to form the light emitting layer. The light output from this organic EL device was 330 cd/m$^2$ when it was driven by a direct bias voltage of 8 volts. The device emitted a greenish blue color.

EXAMPLE XV

This Example illustrates an organic EL device containing a light-emitting layer comprised of a mixture of hydrocarbon compounds. The device was fabricated in accordance with Example VIII except that the light emitting layer described in Step 4 further included a hydrocarbon compound of 9,9-bis[4-(10-phenyl-9-anthryl)phenyl]fluorene. Thus, there were deposited onto the hole transporting layer through simultaneous evaporation 75 parts of 9,9-bis[4-(9-anthryl)phenyl]fluorene at a rate of 0.6 nanometer/second and 25 weight percent or parts of 9,9-bis[4-(10-phenyl-9-anthryl)phenyl]fluorene at a rate of 0.2 nanometer/second from two independently controlled tantalum boats. When driven by a direct bias voltage of 25 mA/cm$^2$, this organic EL device provided a blue emission of about 380 cd/m$^2$.

EXAMPLE XVI

This EL device was fabricated in accordance with Example VIII except that 6,6,12,12-tetramethyl-2,8-diphenylindeno[1,2b]fluorene was used in place of 9,9-bis[4-(9-anthryl)phenyl]fluorene to form the light emitting layer. When driven by a direct bias voltage of 25 mA/cm$^2$, this organic EL device provided a blue emission of about 320 cd/m$^2$.

EXAMPLE XVII

This Example illustrates an organic EL device containing a light-emitting layer comprised of a mixture of hydrocarbon compounds. The device was fabricated in accordance with Example VIII except that onto the hole transporting layer was deposited a 40 nanometers thick light emitting layer through simultaneous evaporation of about 85 weight percent of 6,6,12,12-tetramethyl-2,8-diphenylindeno[1,2b]fluorene at a rate of 0.6 nanometer/second and about 15 weight percent or parts of 9,9-bis[4-(10-phenyl-9-anthryl)phenyl]fluorene at a rate of 0.1 nanometer/second from two independently controlled tantalum boats. When driven by a direct bias voltage of 25 mA/cm$^2$, this organic EL device provided a blue emission of about 370 cd/m$^2$.

Other modifications of the present invention will or may occur to those of ordinary skill in the art subsequent to a review of the present application. These modifications and equivalents thereof are intended to be included within the scope of the present invention.

What is claimed is:

1. An electroluminescent device comprised of an anode, an organic electroluminescent element and a cathode, wherein said electroluminescent element is situated between said anode and said cathode, and contains a fluorescent hydrocarbon component of Formula (II)

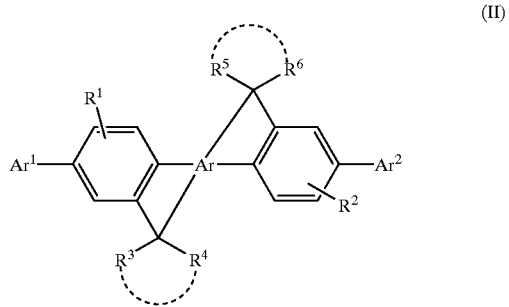

(II)

wherein R$^1$ and R$^2$ are independently selected from the group consisting of hydrogen, an alkyl group, an alicyclic alkyl group, an aryl group, an alkoxy group, a halogen, and a cyano group; R$^3$, R$^4$, R$^5$, and R$^6$ are independently selected from the group consisting of hydrogen, an alkyl group, an alicyclic alkyl group, an aryl group, and an alkoxy group, wherein R$^3$ and R$^4$, or R$^4$ and R$^5$ are optionally combined into a bivalent hydrocarbon group selected from the group consisting of an alkylene, an alkylidene, an alicyclic alkylidene, and an arylalkylidene, wherein Ar$^1$ and Ar$^2$ are independently an aryl group; and wherein Ar is an tetravalent aromatic group.

2. An electroluminescent device in accordance with claim 1, wherein said R$^1$ and R$^2$ are individually selected from the group consisting of methyl, ethyl, cyclohexyl, tert-butyl, methoxy, ethoxy, tert-butoxy, phenyl, tolyl, hydrogen, fluorine, chlorine, and cyano.

3. An electroluminescent device in accordance with claim 1 wherein said R$^3$, R$^4$, R$^5$ and R$^6$ are selected from the group consisting of hydrogen, methyl, ethyl, propyl, hexyl, cyclohexyl, tert-butyl, methoxy, ethoxy, 2-methoxyethyl, phenyl, tolyl, methoxyphenyl, cyclohexylidene, 4-tert-butylcyclohexylidene, benzylidene, and diphenylmethylidene.

4. An electroluminescent device in accordance with claim 1 wherein said Ar$^1$ and Ar$^2$ are selected from the group consisting of an aryl of phenyl, tolyl, tert-butylphenyl, methoxyphenyl, 3,5-diphenylphenyl, 3,5-bis(p-tert-butylphenyl)phenyl, biphenylyl, 4'-methoxybiphenyl-4-yl, 2-phenylvinyl, 2,2-diphenylvinyl, and trans-stilbenyl.

5. An electroluminescent device in accordance with claim 1 wherein R$_1$ to R$_6$ are each a substituent selected from the group consisting of hydrogen, an alkyl group with from 1 to about 6 carbon atoms, an alicyclic alkyl group with from about 3 to about 15 carbon atoms, an alkoxy group with from 1 to about 6 carbon atoms, a dialkylamino group with from about 1 to about 3 carbon atoms, a halogen, and cyano.

6. An electroluminescent device in accordance with claim 1 wherein said substituents for R$_1$ to R$_6$ are individually selected from the group consisting of hydrogen, methyl, ethyl, isopropyl, tert-butyl, cyclohexyl, 4-tert-butylcyclohexyl, methoxy, ethoxy, isopropoxy, tert-butoxy, dimethylamino, diethylamino, fluorine, chlorine, and cyano.

7. An electroluminescent device in accordance with claim 1 wherein said hydrocarbon component is selected from the group consisting of

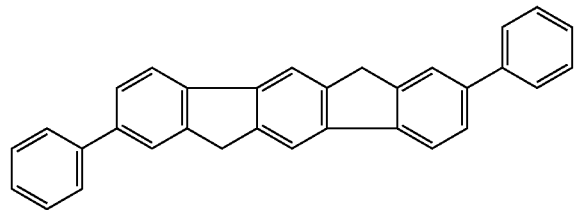

Compound (II-1)

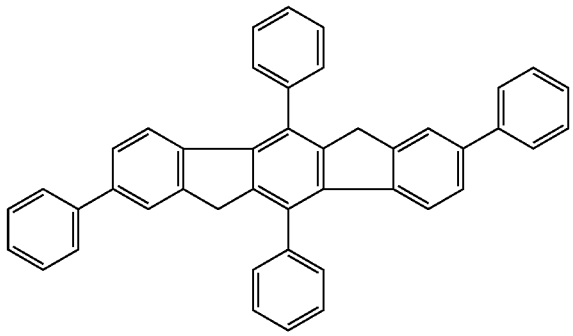

Compound (II-2)

-continued
Compound (II-3)
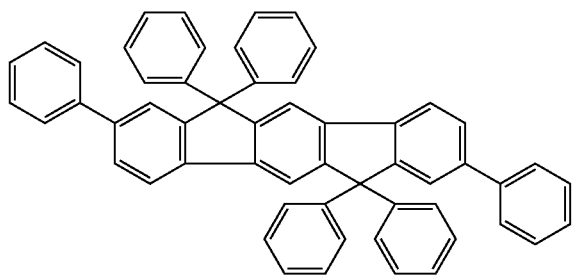
Compound (II-4)
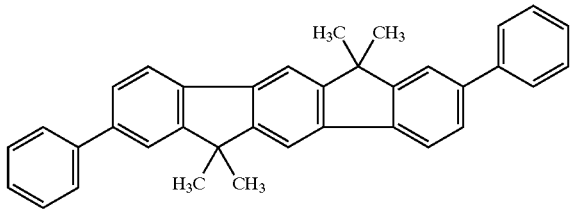
Compound (II-5)
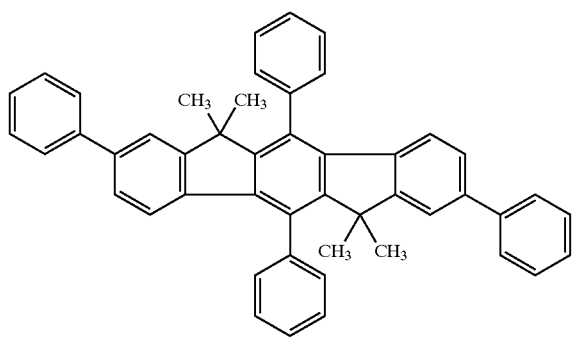
Compound (II-6)
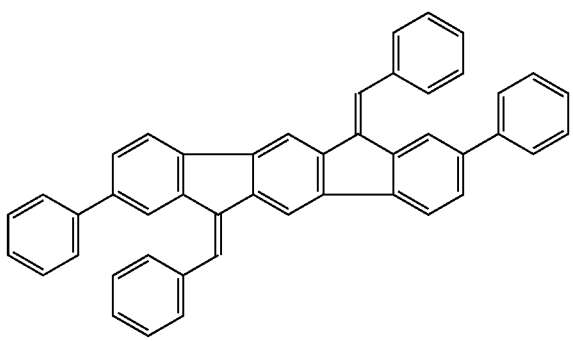
Compound (II-7)
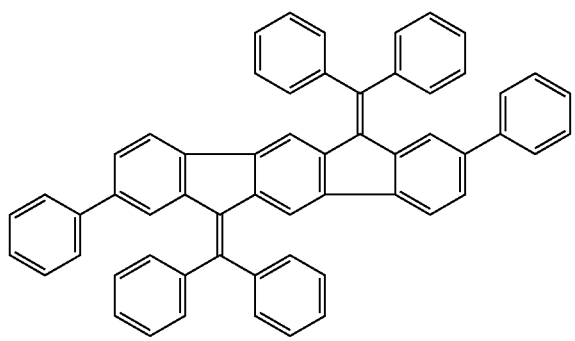
Compound (II-8)
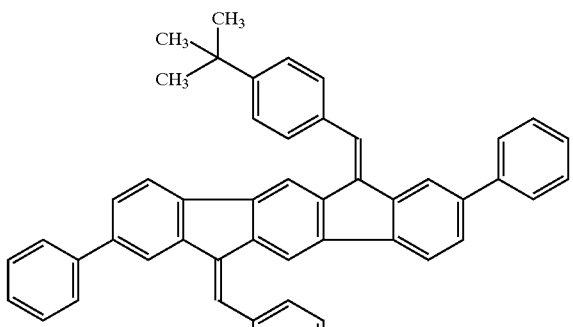
Compound (II-9)

Compound (II-10)
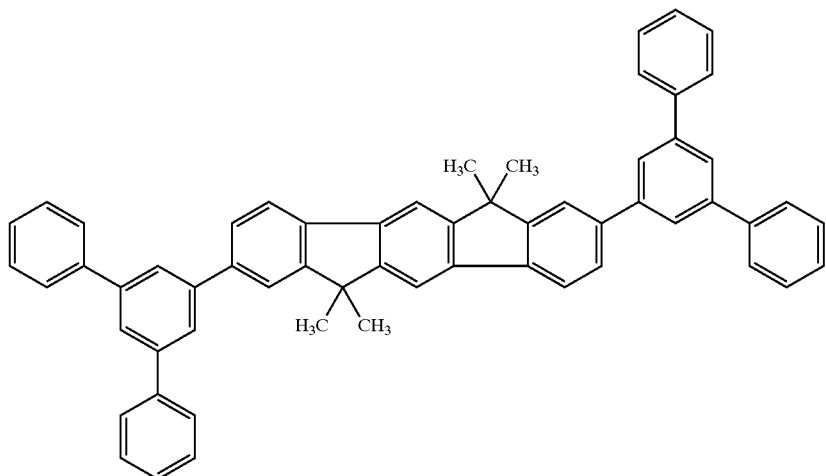
Compound (II-11)
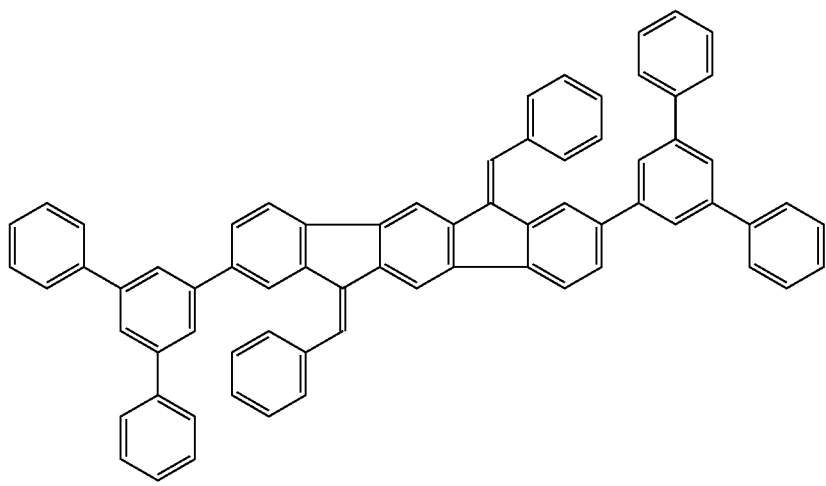
Compound (II-12)
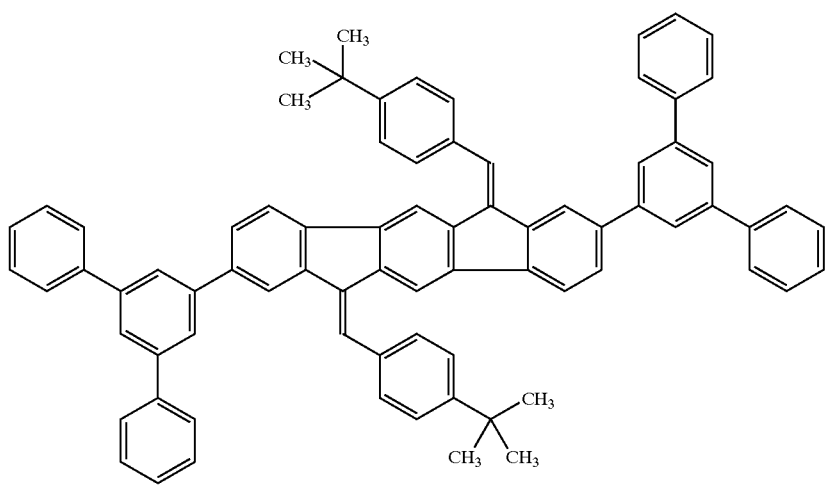

Compound (II-13)
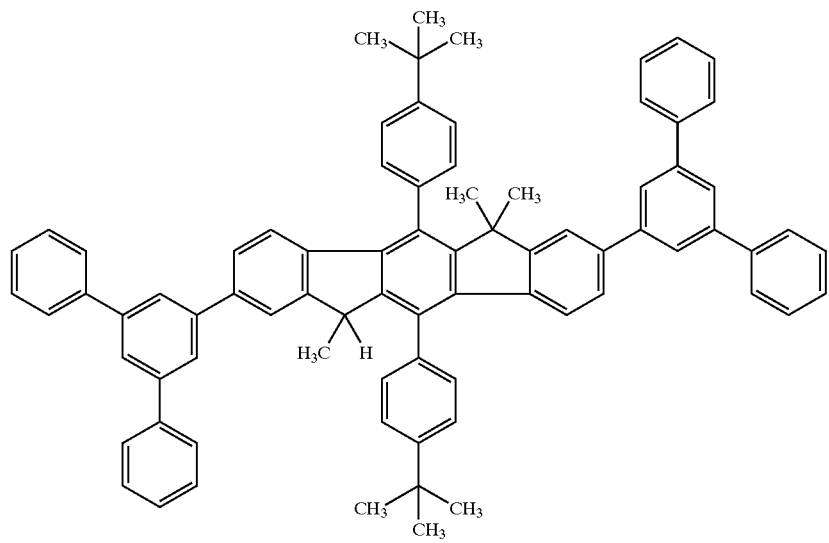
Compound (II-14)
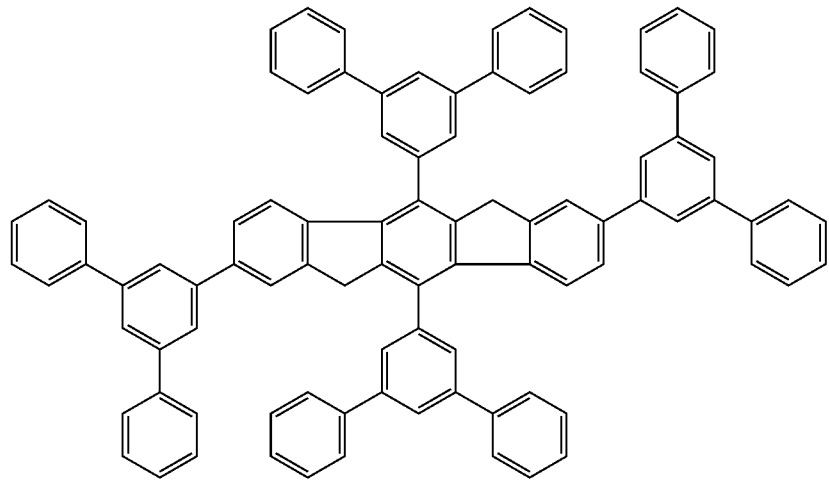
Compound (II-15)
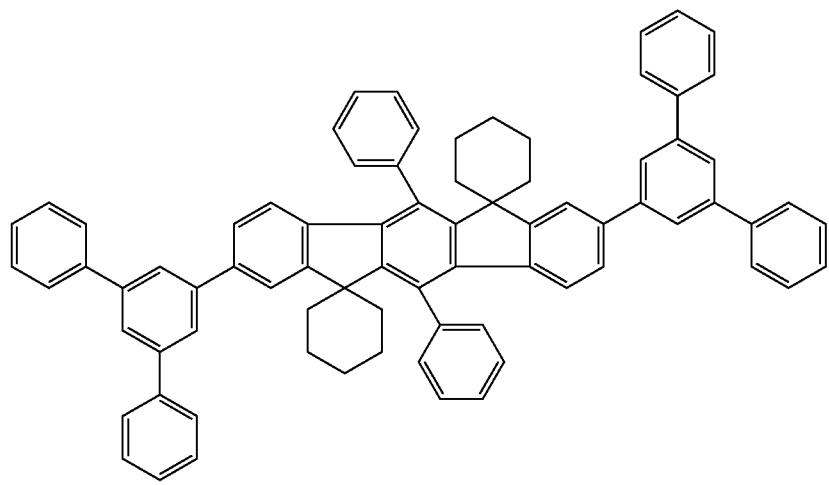

-continued
Compound (II-16)
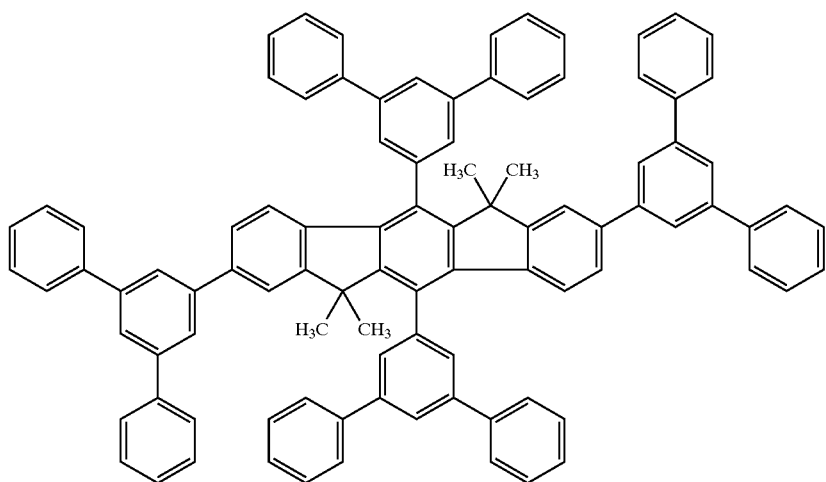
Compound (II-17)
Compound (II-18)
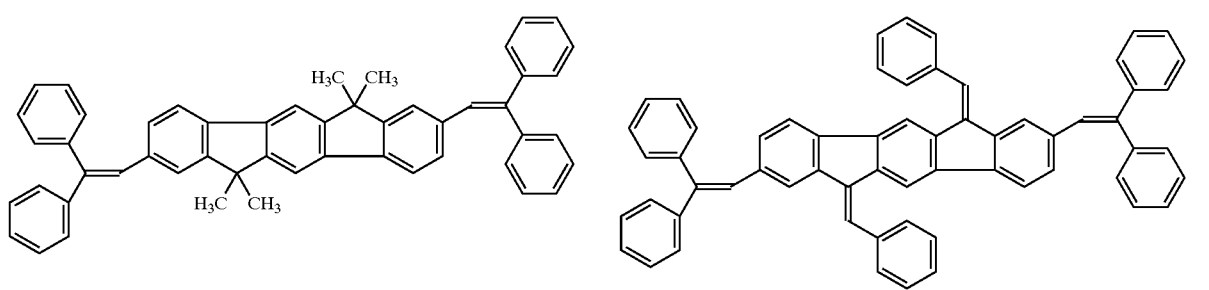
Compound (II-19)
Compound (II-20)
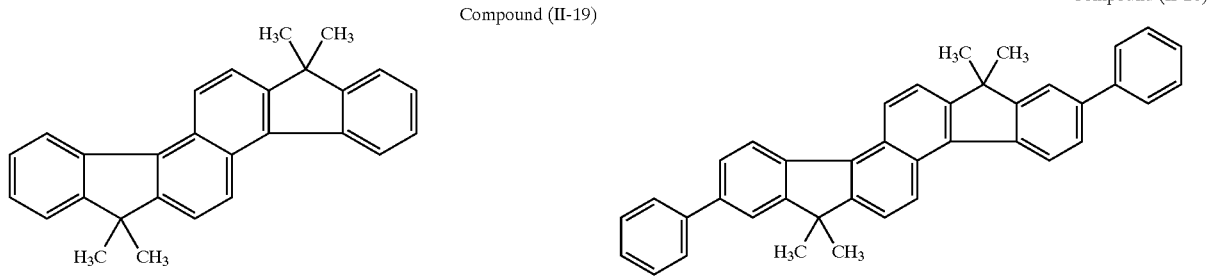
Compound (II-21)
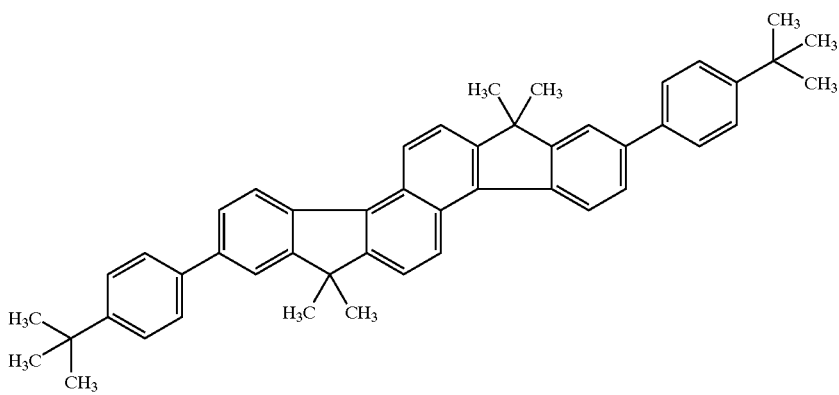

Compound (II-22)
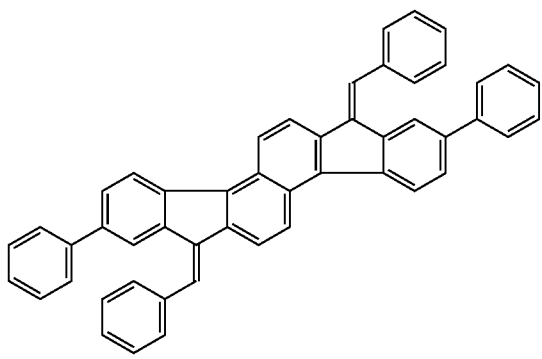
Compound (II-23)
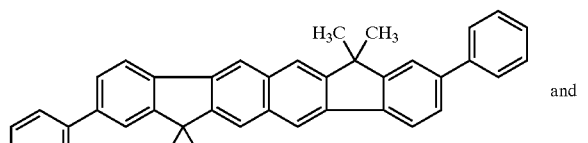
and
Compound (II-24)
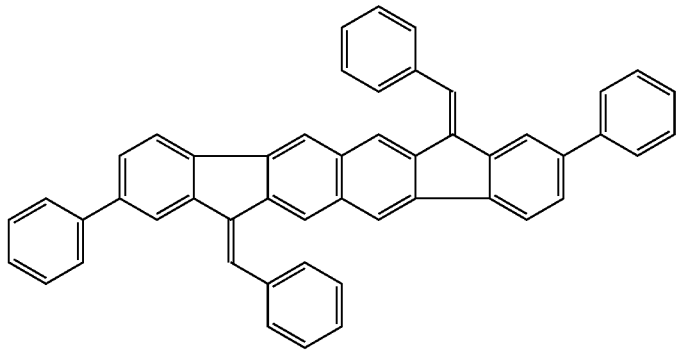
8. An electroluminescent device in accordance with claim 1 wherein $R^1$ and $R^2$ are hydrogen.
9. An electroluminescent device in accordance with claim 8 wherein said hydrocarbon component is selected from the group consisting of
Compound (II-1)
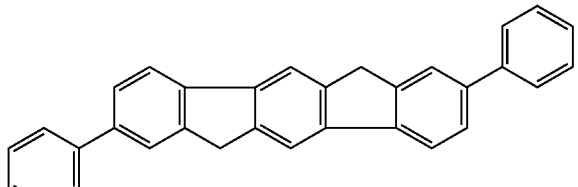
Compound (II-2)
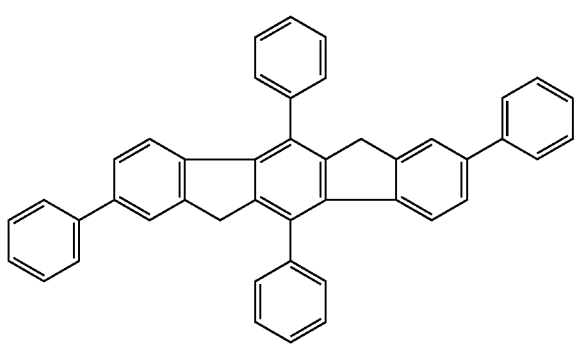
-continued
Compound (II-3)
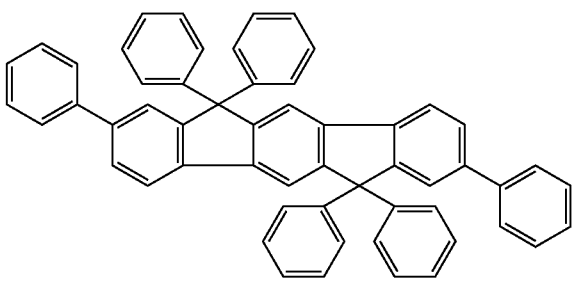
Compound (II-4)
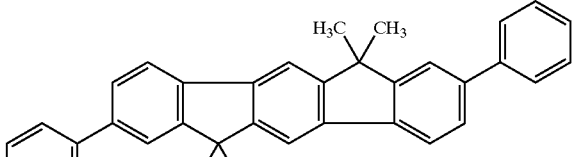
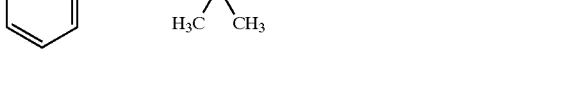

Compound (II-5)

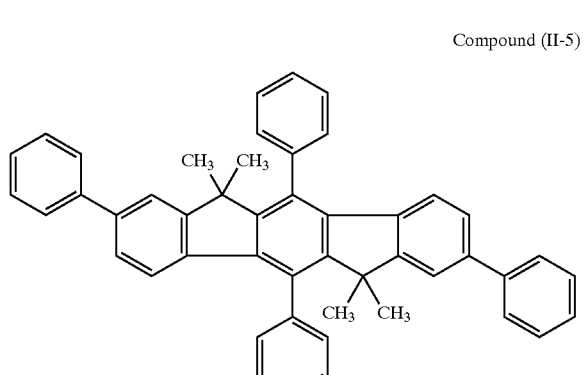

Compound (II-8)

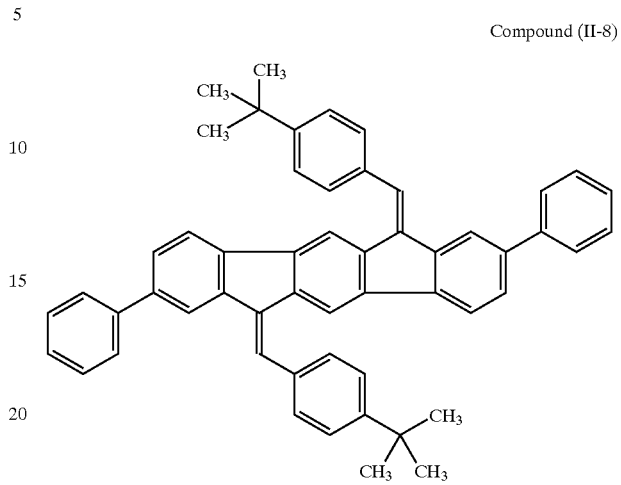

Compound (II-6)

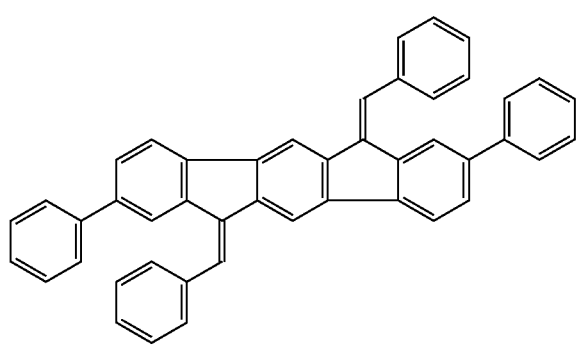

Compound (II-7)

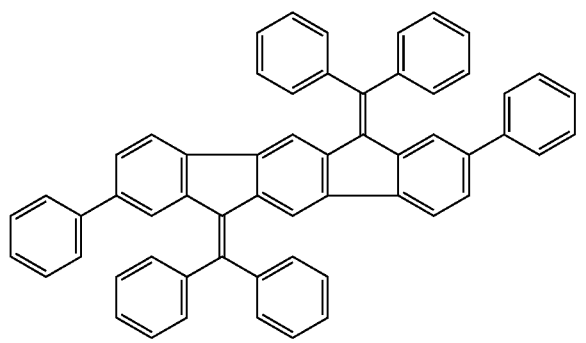

10. An electroluminescent device in accordance with claim 1 wherein said $R^1$ and $R^2$ are methyl or ethyl.

11. An electroluminescent device in accordance with claim 1 wherein said $R^3$, $R^4$, $R^5$ and $R^6$ are selected from the group consisting of hydrogen, methyl, and ethyl.

12. An electroluminescent device in accordance with claim 1 wherein said $Ar^1$ and $Ar^2$ are selected from the group consisting of phenyl, tolyl, tert-butylphenyl, methoxyphenyl, 3,5-diphenylphenyl, 3,5-bis(p-tert-butylphenyl)phenyl, biphenylyl, and 4'-methoxybiphenyl-4-yl, 2-phenylvinyl, and 2,2-diphenylvinyl.

13. An electroluminescent device in accordance with claim 1 wherein $R^1$ to $R^6$ are each a substituent selected from the group consisting of hydrogen, an alkyl group with from 1 to about 6 carbon atoms, and an alicyclic alkyl group with from about 3 to about 15 carbon atoms.

14. An electroluminescent device in accordance with claim 1 wherein said substituents for $R^1$ to $R^6$ are individually selected from the group consisting of hydrogen, methyl, ethyl, isopropyl, tert-butyl, cyclohexyl, 4-tert-butylcyclohexyl, and methoxy.

15. An electroluminescent device in accordance with claim 1 wherein $R^1$ is alkoxy.

16. An electroluminescent device in accordance with claim 1 wherein $R^1$ and $R^2$ are methoxy.

17. An electroluminescent device in accordance with claim 1 wherein $A^2$ is phenyl.

18. An electroluminescent device in accordance with claim 1 wherein $R^1$ and $R^2$ are methyl.

19. An electroluminescent device in accordance with claim 1 wherein $Ar^1$ is phenyl.

20. An electroluminescent device in accordance with claim 1 wherein $Ar^2$ is phenyl.

21. An electroluminescent device in accordance with claim 1 wherein said hydrocarbon component is selected from the group consisting of

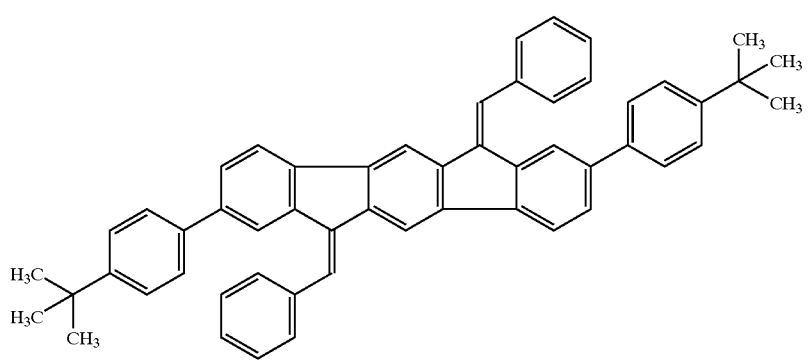
Compound (II-9)
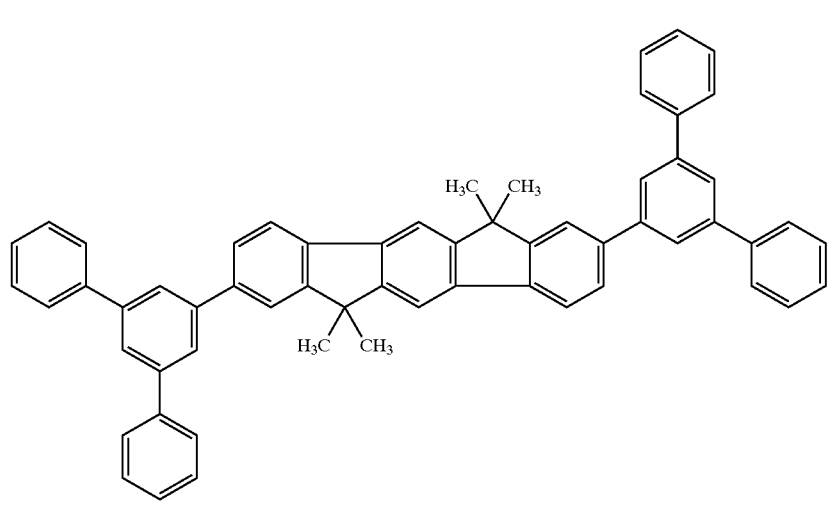
Compound (II-10)
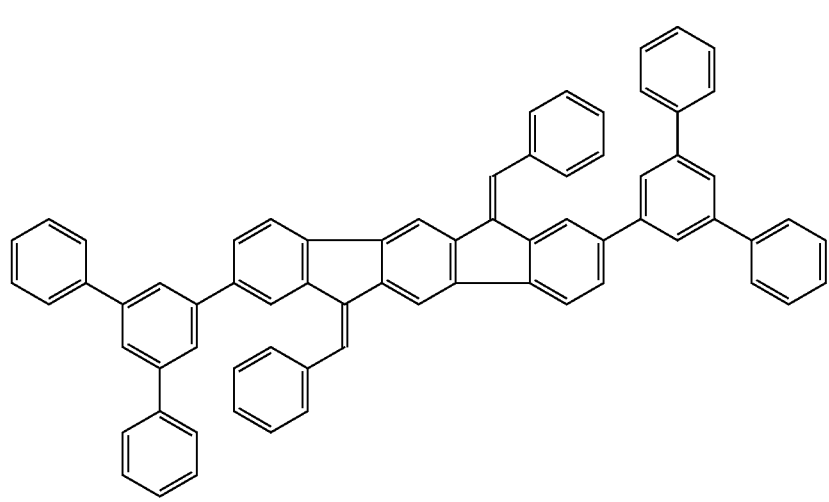
Compound (II-11)

Compound (II-12)
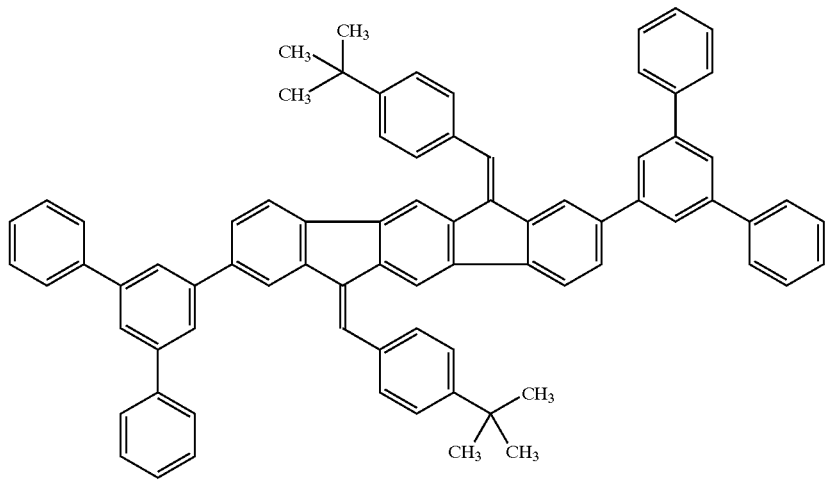
Compound (II-13)
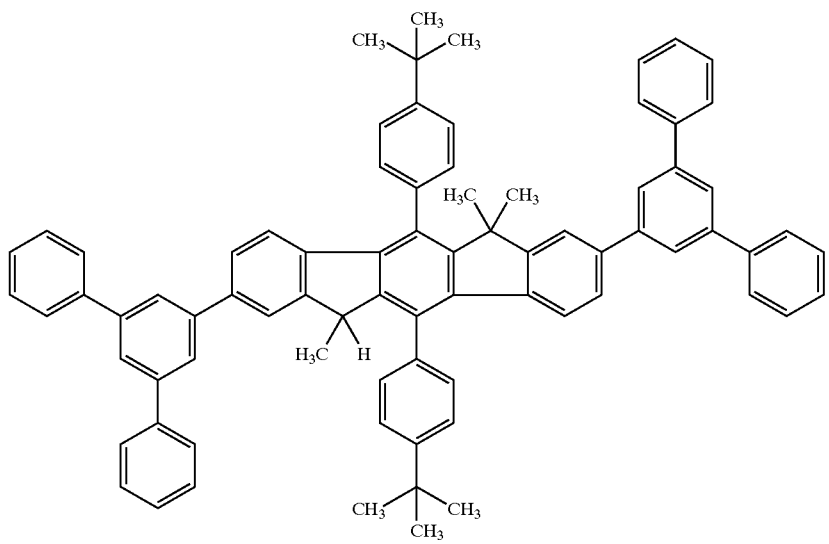
Compound (II-14)
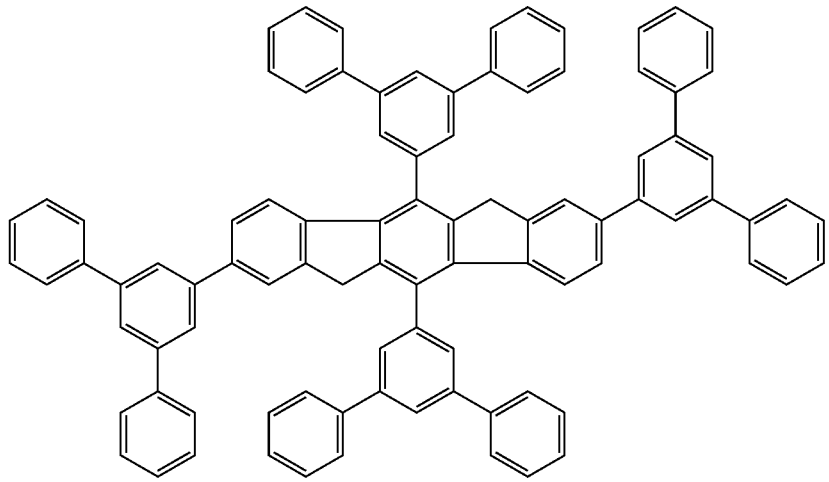

-continued
Compound (II-15)
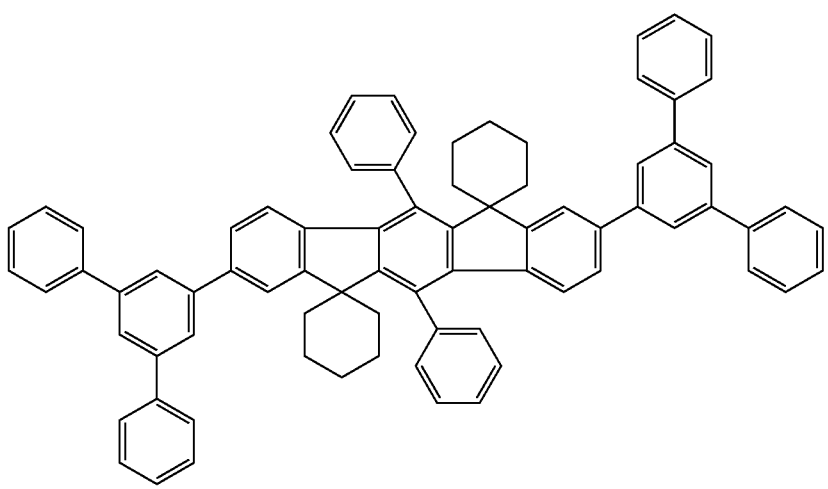
Compound (II-16)
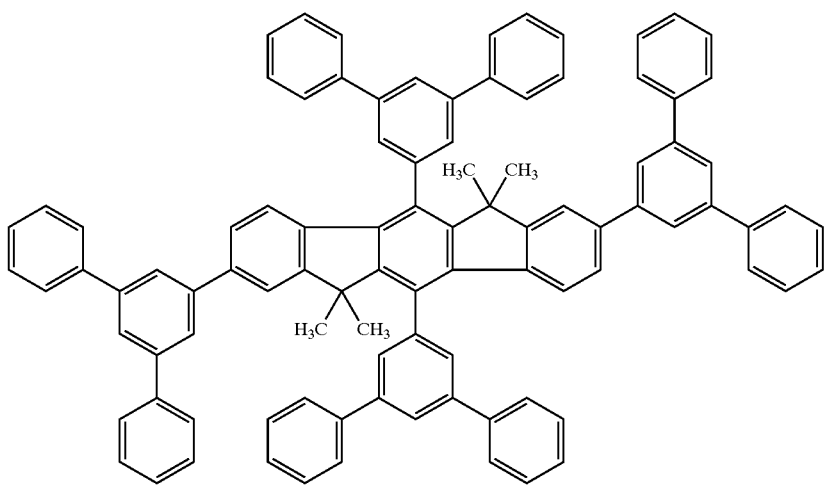
* * * * *